US012163870B2

(12) United States Patent
Jensen et al.

(10) Patent No.: US 12,163,870 B2
(45) Date of Patent: Dec. 10, 2024

(54) METHOD FOR LIQUID ENVIRONMENT MONITORING AND LIQUID ENVIRONMENT MONITORING SYSTEM

(71) Applicant: Ejlskov A/S, Aarhus N (DK)

(72) Inventors: Palle Ejlskov Jensen, Aarhus N (DK); Ivan Yélamos Vela, Aarhus N (DK); Jens Elmose, Aarhus (DK)

(73) Assignee: EJLSKOV A/S, Aarhus N (DK)

( * ) Notice: Subject to any disclaimer, the term of this patent is extended or adjusted under 35 U.S.C. 154(b) by 561 days.

(21) Appl. No.: 17/294,374

(22) PCT Filed: Nov. 19, 2019

(86) PCT No.: PCT/DK2019/050356
§ 371 (c)(1),
(2) Date: May 14, 2021

(87) PCT Pub. No.: WO2020/103992
PCT Pub. Date: May 28, 2020

(65) Prior Publication Data
US 2022/0011198 A1   Jan. 13, 2022

(30) Foreign Application Priority Data

Nov. 19, 2018 (DK) .......................... PA 2018 70758
Nov. 19, 2018 (DK) .......................... PA 2018 70760

(51) Int. Cl.
*G01N 1/12* (2006.01)
*G01N 1/14* (2006.01)
(Continued)

(52) U.S. Cl.
CPC ............... *G01N 1/12* (2013.01); *G01N 1/405* (2013.01); *G01N 2030/009* (2013.01)

(58) Field of Classification Search
CPC ........ B01D 15/08; B01D 29/01; B01D 29/66; B01D 35/02; G01N 1/00; G01N 1/10;
(Continued)

(56) References Cited

U.S. PATENT DOCUMENTS 6,306,350 B1 * 10/2001 Mereish ................. G01N 33/18
73/863.25
7,059,206 B1    6/2006 Kingston et al.
(Continued)

FOREIGN PATENT DOCUMENTS

CN    108802321 A    11/2018
EP      1010974 A1     6/2000
(Continued)

OTHER PUBLICATIONS

Abaroa-Perez, B. et al. "In Situ Miniaturised Solid Phase Extraction (m-SPE) for Organic Pollutants in Seawater Samples." Journal of Analytical Methods in Chemistry. Apr. 2, 2018.

*Primary Examiner* — Brandi N Hopkins
(74) *Attorney, Agent, or Firm* — Schmeiser, Olsen & Watts LLP

(57) ABSTRACT

Various aspects of the present disclosure are directed to methods and systems for in-situ accumulation of one or more substances from a liquid environment. In one embodiment of the present disclosure, a method is disclosed including placing a cartridge with a sorbent in the liquid environment, driving a liquid volume through the sorbent, and repeating the act of driving as a function of time.

13 Claims, 19 Drawing Sheets

(51) Int. Cl.
*G01N 1/40* (2006.01)
*G01N 30/00* (2006.01)
*G01N 33/18* (2006.01)

(58) Field of Classification Search
CPC ............ G01N 1/12; G01N 1/34; G01N 30/00;
G01N 33/18; G01N 1/14; G01N 1/22;
G01N 1/28; C02F 1/00
See application file for complete search history.

(56) References Cited

U.S. PATENT DOCUMENTS

| | | | |
|---|---|---|---|
| 7,992,430 B2* | 8/2011 | de Jonge | E21B 49/08 |
| | | | 73/61.59 |
| 2006/0043022 A1 | 3/2006 | Wada et al. | |
| 2009/0007704 A1 | 1/2009 | Bowers et al. | |
| 2012/0164750 A1* | 6/2012 | Gjerde | G01N 1/405 |
| | | | 436/178 |
| 2018/0202902 A1 | 7/2018 | Hoffarth et al. | |

FOREIGN PATENT DOCUMENTS

| | | |
|---|---|---|
| WO | 2005098391 A1 | 10/2005 |
| WO | 2015150429 A2 | 10/2015 |
| WO | 2016/011385 A1 | 1/2016 |
| WO | 2017189713 A2 | 11/2017 |

\* cited by examiner

METHOD FOR LIQUID ENVIRONMENT MONITORING AND LIQUID ENVIRONMENT MONITORING SYSTEM

CROSS-REFERENCE TO RELATED APPLICATIONS

This application is a national stage filing based upon International PCT application no. PCT/DK2019/050356, filed 19 Nov. 2019, which claims the benefit of priority to Denmark application no. PA 2018 70758, filed 19 Nov. 2018, and Denmark application no. PA 2018 70760, filed 19 Nov. 2018.

FIELD OF THE INVENTION

The present invention relates to a method for in-situ accumulation of one or more substances from a liquid environment.

The present invention relates to a system for in-situ accumulation of substance in a liquid environment.

BACKGROUND OF THE INVENTION

At present, there are methods performed by systems on the market capable of measuring pollution in a liquid environment, such as a sea, a river, a lake, a ground water reservoir or wetted soil.

Some of these methods use solid phase extraction (SPE), where a sorbent is positioned subsurface and liquid is forced through the sorbent. The pollution may then be absorbed by or adsorbed to the sorbent.

The methods using solid phase extraction can be divided into two kinds of methods: an active method where a system performs work on a liquid for driving the liquid through the sorbent, and a passive method where a liquid is driven through the sorbent without actively performing work on the liquid.

The active methods use a pump for pumping liquid through the sorbent. The pumps make the active methods expensive and the energy consumption high. Therefore, the active methods are limited by the size of the battery, which determines the maximum sampling period. The active methods utilise equipment which must often be serviced and the battery replaced or recharged.

The passive methods comprise means for passively determining the flow through the sorbent. The means are in some methods a tracer arranged next to the sorbent. The tracer leaches at a rate proportional to passing water. However, as the tracer leaches the resistance experienced by the water passing through the cartridge decreases resulting in an increased rate of passing water. The result being that the last part of the sampling period has a higher water rate than the first part of the sampling period, and this causes a significant increase of statistical uncertainty. Furthermore, this negative effect increases with total sampling time as the difference in integrated water volume of the first part of the sampling time and of the last part of the sampling time increases when changing total sampling time from one day to two days.

Neither the passive methods nor the active methods are capable of having a sampling period of a month without service. Because the active systems have too high a power consumption and the passive systems have a water rate which gradually increases over the sampling period.

There are several systems on the market capable of measuring pollution in a liquid environment, such as a sea, a river, a tube, a lake, a ground water reservoir or wetted soil.

Some of these systems use a solid phase extraction (SPE), where a sorbent in a cartridge is positioned subsurface and liquid is forced through the sorbent. The pollution may then be absorbed by or adsorbed to the sorbent.

The solid phase extraction systems can be divided into two kinds of systems: an active system and a passive system.

The active systems comprise a pump for pumping liquid through the sorbent. The problem is that these pumps are expensive and energy consuming. Therefore, the active systems are limited by the size of the battery, which determines the maximum sampling period, and the active systems must often be serviced and the battery replaced.

The passive systems comprise means for passively determining the flow through the sorbent. The means may be a tracer arranged next to the sorbent. The tracer leaches at a rate proportional to passing water. However, as the tracer leaches the resistance experienced by the water passing through the cartridge decreases resulting in an increased rate of passing water. The result being that the last part of the sampling period has a higher water rate than the first part of the sampling period, which causes a significant statistical uncertainty. Furthermore, this negative effect increases with the total sampling time, because the difference in integrated water volume from the first part of the sampling time to the last part of the sampling time increases when changing the total sampling time from a day to two days.

Neither the passive systems nor the active systems are capable of having a sampling period of a month without service, because the active systems have too high a power consumption and the passive systems have a water rate which gradually increases over the sampling period.

OBJECT OF THE INVENTION

It is a first object of the invention to overcome the limitations of the prior art by providing a method which is energy efficient and capable of repeatedly performing acts of driving precise liquid volumes through a sorbent.

It is a second object of the invention to overcome the limitations of the prior art by providing a system which is energy efficient and capable of repeatedly performing precise measurements.

DESCRIPTION OF THE INVENTION

An object of the invention is achieved by a method for in-situ accumulation of one or more substances from a liquid environment. The method may comprise acts of:
   placing a cartridge with a sorbent in the liquid environment;
   driving a liquid volume through the sorbent;
   repeating the act of driving as a function of time.

Thereby, the sorbent will accumulate one or more substances each time an act of driving a liquid volume through the sorbent is performed, because substances in the liquid may be absorbed or adsorbed by the sorbent when the liquid volume passes through the sorbent. The sorbent or the cartridge with the sorbent may afterwards be sent to a laboratory and tested. The accumulated liquid volume through the sorbent is known, and thus an average amount of the one or more substances in the accumulated liquid volume can be calculated and compared with allowed threshold values.

The sorbent may be adapted for accumulating a specific substance or a specific group of substances.

The sorbent may be adapted for accumulating nitrates, phosphates, oils, pesticides or pharmaceuticals. The sorbent may be adapted for accumulating other substances.

The sorbent may be a solid-phase extraction sorbent sold by companies such as Waters or Merck.

The sorbent may be a different kind of sorbent sold by other or the same companies.

The act of placing a cartridge with a sorbent in the liquid environment is performed by placing the cartridge in a sea, a river, a lake, a drilled bore, a ground water reservoir or any other liquid environment.

The act of driving a liquid volume through the sorbent ensures that the sorbent has accumulated substances from the liquid volume driven through the sorbent.

The act of repeating the act of driving as a function of time enables the method to perform over a time period of 0.1-3 months, 0.5-2 months or 0.75-1.5 months, or 1 month, because the function of time may be adapted to enable the method to be performed over a long period of time.

The amount of liquid which can pass through a sorbent before the sorbent becomes saturated or inactive depends the sorbent and the amount of the sorbent in the cartridge, thus each sorbent has an accumulated liquid volume limit.

If the method is to be performed over a month and the sorbent has an accumulated liquid volume limit, then the acts of driving the liquid volume through the sorbent may be adapted, such that the act of driving can be repeated 100 times before reaching the accumulated liquid volume limit.

The function of time may then be adapted such that the act of driving is repeated with a period, such as every 7.2 hours.

The function of time may be adapted such that the act of repeating is performed in the hours between 4 PM and 8 AM to determine whether a factory, a plant, or a wastewater treatment plant pollutes after hours.

The leaching time of pollution from a polluter into a river, a sea or a lake, is generally very short. The leaching time of pollution may only be six hours or less. Thus, the method must perform an act of driving a liquid volume through the sorbent when the pollution is measurable.

The function of time may randomly distribute the acts of repeating or semi-randomly distribute the acts of repeating.

In an embodiment of the method, the cartridge is in liquid connection with a chamber, wherein the liquid volume is driven through the sorbent into the chamber, and thereby the liquid volume can be controlled by controlling a volume of the chamber.

The liquid may be water or substantially be water.

The liquid may comprise water.

In an embodiment, the method is for in-situ accumulation of one or more substances from a fluid environment. The method may comprise acts of:

placing a cartridge with a sorbent in the liquid environment;
driving a fluid volume through the sorbent;
repeating the act of driving as a function of time.

Thereby, the method can be used to accumulating one or more substances from a fluid environment.

In an aspect of the invention, the act of driving may be performed by changing a volume of a chamber having an initial chamber volume in a liquid connection with the cartridge.

The change in volume from the initial chamber volume causes the pressure in the chamber to change relative to the liquid environment. The pressure change will drive a liquid volume through the sorbent until there is no pressure difference between the chamber and the liquid environment.

The pressure in the chamber and the liquid environment is equalised when a fluid volume equal to the change in the chamber volume has been driven through the sorbent. Thereby, a well-determined fluid volume is driven through the sorbent as the chamber volume can be controlled precisely.

The initial chamber volume may be zero or close to zero and the chamber volume may be changed by a volume equal to the desired fluid volume.

The initial chamber volume may be equal to the desired fluid volume and the chamber volume may be changed to zero.

In an aspect of the invention, the act of driving is performed by increasing the chamber volume of the chamber.

The increase in the chamber volume causes a negative pressure in the chamber relative to the fluid environment. The negative pressure performs the act of driving the fluid volume through the sorbent.

The negative pressure caused by the increase in the chamber volume affects the sorbent uniformly, and the liquid flow through the sorbent is therefore uniformly distributed affecting the ability of the sorbent to accumulate substances.

The pressure in the chamber and the liquid environment is equalised when a fluid volume, equal to the change in the chamber volume, has been driven through the sorbent.

Thereby, a well-determined fluid volume is driven through the sorbent because the chamber volume can be controlled precisely.

In an aspect of the invention, the act of driving may be performed by a pressure difference at the chamber relative to the liquid environment while the chamber has a fixed chamber volume.

Thereby, the method performs the act of driving semi-passively, because the method actively changes the chamber volume, and the pressure difference performs the work on the liquid, thereby driving the liquid volume through the sorbent.

The method may perform an act of hibernating while the chamber has the fixed chamber volume until the chamber volume is filled with liquid.

The time needed for the chamber to be filled depends on various factors, such as the change in volume, the sorbent and the amount of sorbent and the density of the sorbent as well as other factors.

Experiments have shown that if the change in volume is +8 mL, then for many sorbents the time it takes to fill the +8 mL is 5-15 min. The skilled person would be able to test the time needed to fill any volume using any sorbent.

The method may perform an act of hibernating for 20 min after increasing the chamber volume.

In an aspect of the invention, the act of driving includes an act of resetting the chamber to the initial chamber volume.

This makes easier to control the liquid volume and the chamber can be smaller compared to a method which does not reset the chamber volume between each act of driving.

Furthermore, the initial chamber volume may be zero or close to zero. Any residual liquid in the chamber makes it more difficult to control the change of the chamber volume and it may cause the chamber volume and the change in the chamber volume to drift between acts of repeating the act of driving.

The liquid in the chamber may be expelled from the chamber through an exhaust in the liquid connection between the cartridge and the chamber. The exhaust may have a one way exhaust valve such that all the liquid in the chamber is expelled from the chamber through the exhaust, while ensuring that liquid enters the chamber through the cartridge.

In an aspect of the invention, the act of repeating includes an act of hibernating as a function of time between the acts of driving.

The method is energy efficient because the act of hibernating between the acts of repeating the act of driving a fluid volume through the sorbent results in low energy consumption.

In an aspect of the invention, the act of hibernating is performed for a hibernation time being between 0.1-24 hours, 0.1-10 hours, 0.5-5 hours, 0.75-3.5 hours, or 1-2 hours.

The hibernation time depends on the function of time, which determines when the act of driving is performed.

The method is capable of measuring over a long period of by performing an act of hibernating for a hibernation time which may be long.

In an aspect of the invention, the method is performed over a period of 0.1-3 months, 0.5-2 months or 0.75-1.5 months, or 1 month.

Thereby, the method makes it harder for a polluter to hide pollution, because the method measures pollution randomly for long periods of time.

An object of the invention is achieved by a system for in-situ accumulation of substances. The system may have a cartridge with a sorbent and means adapted to execute one or more of the previously described acts.

The system may have means to drive a liquid volume through the sorbent.

Thereby the system may perform the efficient method capable of repeating acts of driving a liquid volume through the sorbent.

In an aspect of the invention, the system may comprise:
- a frame arrangement supporting an actuator configured to drive a spindle defining a displacement axis, the spindle is coupled to;
- a flange for a displacement along the displacement axis, the flange supporting a piston crown configured to operate in;
- a chamber defining a chamber volume as a function of the piston crown, the chamber having means for being fixed to the frame arrangement. The chamber may be in a liquid connection with the cartridge.

When turning the spindle, the piston crown changes the chamber volume, and the change of the chamber volume enables driving a liquid volume through the sorbent when the cartridge is placed in a liquid environment.

Thereby, the system will drive a liquid volume equal to the change in chamber volume through the sorbent. The total liquid volume through the sorbent is the accumulated liquid volume, which will increase when repeatedly driving a liquid volume through the sorbent The change in the chamber volume is proportional to the rotation of the spindle. The rotation of the spindle causes the flange to be displaced along the displacement axis and thus the piston crown will be displaced along the displacement axis.

The piston crown defines an end of a piston. The piston crown may be supported to the flange by a piston shaft extending from the flange to the piston crown. The piston shaft may extend parallel to the displacement axis as this will cause the displacement of the flange to be equal to the displacement of the piston crown relative to the displacement axis. Thereby, the precision of the system increases as there is a direct correlation between the rotation of the spindle and the change in volume.

The piston may be secured to the flange by a piston foot adapted for engaging with the flange.

The piston foot may be secured to the flange by gluing the piston foot to the flange or by screwing a screw through the piston foot into the flange. Unwanted displacement of the piston, and thus the piston crown, is limited as a function of the connection between the piston and the flange.

In an embodiment, the piston foot is secured to the flange by two screws on each side of the piston shaft, thereby limiting unwanted displacement and increasing the precision of the system.

Any displacement, which is not parallel to the displacement axis, decreases precision. In severe cases unwanted displacement may cause the liquid connection between the cartridge and the chamber to be broken.

The system may be arranged such that liquid is present on both sides of the flange relative to the displacement axis such that the flange is exposed to the same pressure and thus the same force on both sides of the flange. The effect is that the precision of the displacement of the flange increases significantly, which will result in more precise measurements.

The chamber may comprise a chamber channel adapted for displacement of the piston crown parallel to the displacement axis while forming a liquid-tight connection with the piston crown, such that liquid may only enter and exit the chamber through the liquid connection.

The piston crown may be equipped with one or more piston rings for increasing the liquid-tight connection between the liquid crown and the chamber, while the one or more piston rings have a sufficiently low friction, such that the piston crown may be displaced.

The piston crown has two positions that define a minimum chamber volume and a maximum chamber volume. The chamber has its minimum chamber volume when a distance between the liquid connection and the piston crown is at a minimum.

The minimum chamber volume may be zero or close to zero because it is easier to control compared to having a minimum chamber volume different from zero. Thereby, drift of the change in volume is prevented or at least minimised and this decreases the uncertainty which would otherwise increase significantly over several acts of driving a single liquid volume through the sorbent.

The chamber has its maximum chamber volume when the distance between the liquid connection and the piston crown is maximised while the piston crown is still firmly connected to the chamber. The skilled person would by trial and error be able to determine the maximum chamber volume for a specific system design or for specific chamber and piston designs.

The system may, when placed in a liquid environment, perform an act of driving a single liquid volume by displacing the piston crown in the chamber having an initial chamber volume, such that the volume of the chamber increases. The chamber is through the liquid connection with the cartridge connected to the liquid environment and the increase in volume will cause a negative pressure at the chamber relative to the liquid environment. The negative pressure is the driving force for driving liquid through the cartridge and the sorbent into the chamber until there is no pressure difference between the chamber and the liquid environment. This ensures that the volume of the liquid volume is equal to the change in volume of the chamber. The change in volume of the chamber can be controlled reliably and precisely.

Thus, the system removes or at least significantly decreases the drift in the size of liquid volume, thus the first liquid volume driven through the sorbent is equal to or at least almost equal to the $100^{th}$ liquid volume driven through the sorbent.

The liquid in the chamber may afterwards be removed by resetting the piston crown, such that the chamber has the initial chamber volume. This will cause the liquid to be pushed out of the chamber and through the cartridge.

The initial chamber volume may be zero or close to zero.

The skilled person would realize that the system is only active and only consumes energy when displacing the piston crown. The system is passive while the liquid drives through the sorbent and into the chamber, thereby the system is energy efficient because the displacement of the flange and the piston crown is not energy demanding.

Thus, the system is able to repeatedly drive precise liquid volumes through the sorbent in an energy-efficient manner.

The system may be hibernating while the chamber is filled with liquid for reducing idle power consumption.

The low energy consumption and reliable system enable accumulation of one or more substances over a time period of 0.5-2 months without service, which is not possible today. The system may perform 50-200 acts of driving a liquid volume through the sorbent over the period of 0.5-2 months.

The cartridge may comprise an inlet in direct contact with the liquid environment, when in intended use.

The cartridge may comprise an outlet connected to the liquid connection, and the sorbent is arranged between the inlet and the outlet.

In an embodiment, the sorbent may be positioned near the outlet for limiting the amount of residual liquid between the sorbent and the liquid connection.

Furthermore, if the sorbent is positioned near the inlet and the system is placed in a river with a strong current, then the residual liquid may be dragged out through the sorbent by the current. This would cause a drop in pressure between the sorbent and the liquid connection causing an uncontrolled movement of liquid through the sorbent, thereby the precision is lowered significantly.

The sorbent in the cartridge may be an adsorbent or an absorbent.

The sorbent may be adapted for accumulating a specific substance or a specific group of substances.

The sorbent may be adapted for accumulating nitrates, phosphates, oils, pesticides or pharmaceuticals. The sorbent may be adapted for accumulating other substances.

The sorbent may be a solid-phase extraction sorbent sold by companies such as Waters or Merck.

The sorbent may be a different kind of sorbent sold by other or the same companies.

The sorbent may afterwards be removed from the system and analysed in a laboratory.

The chamber is fixed to the frame arrangement to ensure that the displacement of the flange causes the piston crown to be displaced in the chamber without any uncontrolled displacement of the chamber as this would cause a drift in the liquid volume and thereby cause the liquid volume to differ uncontrollably between each act of driving a liquid volume through the sorbent.

The chamber may be fixed by columns extending from the frame arrangement to the chamber.

The frame arrangement may comprise a shell extending in the general direction of the spindle. The shell may at least partially surround the spindle, the flange, the chamber and the cartridge. The chamber may have means for being fixated to the shell.

In an embodiment, the shell surrounds the spindle, the flange, the chamber and the cartridge.

Both embodiments of the shell protect the mechanical parts of the system from fish, strong currents or objects moved by the currents.

The shell must not seal the system from the liquid environment and therefore the shell may have diffusion gaps for diffusion of the liquid in the liquid environment.

In an embodiment the system is adapted for in-situ accumulation of substances in a fluid environment. Thereby, the use of the system is increased.

In an aspect of the invention, the system may comprise a chamber plate fixed to the frame arrangement. The chamber plate is adapted for securing the chamber.

The chamber plate makes it easier to secure the chamber plate to the frame arrangement as the chamber plate can be secured at two or three or more points to the frame arrangement. Thereby, drift of the liquid volume is decreased and the system becomes more reliable.

The chamber plate may be secured to the chamber by gluing or by screws or a friction member.

The chamber plate may have a chamber aperture for insertion of the chamber.

The chamber aperture may have a friction member for securing the chamber.

In an embodiment, the system may comprise a first chamber plate and a second chamber plate and the chamber comprises chamber wings. The first chamber plate and the second chamber plate are secured to the chamber by clamping the chamber wings.

The first chamber plate and the second chamber plate may have two, three or more male connections for connecting with the shell having corresponding first and second chamber plate channels, each having a lock arrangement for limiting the movement of the chamber plates.

Tests have shown that this particular embodiment is mechanically stable over time and the embodiment also makes it easy to change the different mechanical components as there is no need for screwing or unscrewing.

In an aspect of the invention, system comprises two or more piston crowns, a two or more chambers, and two or more cartridges positioned symmetrically around the displacement axis.

The force on the flange will be distributed evenly when positioning the piston crowns, the chambers and the cartridges are positioned symmetrically relative to the displacement axis. Thereby the flange to moves precisely with little to no twisting or flexing, when comparing the system to a system having only a single piston crown, a single chamber and a single cartridge.

The two or more cartridges are connected to the two or more chambers by two or more liquid connections, and the two or more cartridges comprise two or more sorbents.

In an aspect of the invention, the system may comprise two or more piston crowns and two or more corresponding chambers defining two or more chamber volumes as two or more functions of the two or more the piston crowns; and two or more cartridges, wherein the piston crowns, the chambers, and the cartridges are arranged to establish force symmetry relative to the displacement axis.

The two or more chambers and two or more the corresponding piston crowns may define two or more chamber volumes, which may be defined from two different functions of the displacement of the piston crowns. Thus, two chambers having piston crowns with the same displacement may have two different chamber volumes. This will cause a difference in the negative pressure in each chamber relative to the fluid environment and the flange will therefore experience two different forces. This difference may be mitigated by arranging the piston crowns, the chambers, and the cartridge to established force symmetry. Thereby, the system is enabled to drive different liquid volumes through the sorbents without compromising the reproducibility of each act of driving liquid volumes through the sorbents.

The two or more cartridges are connected to the two or more chambers by two or more liquid connections and the two or more cartridges comprising two or more sorbents.

In an aspect of the invention, the spindle may be connected to the flange by a ball screw. The ball screw will reduce slackness between the spindle and the flange. This will increase the precision of the displacement of the flange and this is important when performing 50-200 measurements without service.

In an aspect of the invention, the flange may comprise a neck extending perpendicularly from the flange towards the actuator. The neck comprises an internal thread adapted to engage with an end of the spindle.

There is a correlation between the length of the neck and the precision of the flange movement.

The neck may be the only stabilising part.

In an embodiment, the neck will be close to the frame arrangement when the chamber has the maximum chamber volume.

The system may comprise a battery for powering the actuator, such that the system may be a single unit.

In an aspect of the invention, the liquid connection comprises an exhaust adapted for expelling liquid from the chamber.

In an aspect of the invention, the liquid connection may comprise an exhaust adapted for expelling fluid from the chamber. This will reduce the amount of liquid expelled back through the cartridge and sorbent and the pressure on the sorbent is decreased reducing the risk of the sorbent being pushed out of the cartridge when expelling liquid from the chamber.

The exhaust may be equipped with a one-way exhaust valve, such that liquid does not enter the chamber when there is a negative pressure in the chamber relative to the liquid environment, thus increasing the precision of the fluid volume passing the sorbent.

The liquid connection may further be provided with a one-way cartridge valve, such that when expelling liquid from the chamber, then the liquid is only expelled through the exhaust.

In an embodiment, the liquid connection may comprise an exhaust with a one-way exhaust valve, such that liquid does not enter the chamber when there is a negative pressure in the chamber relative to the liquid environment, and the liquid connection may also comprise a one-way cartridge valve, such that when expelling liquid from the chamber then the liquid is only expelled through the exhaust.

An object of the invention is achieved by a computer program comprising instructions to cause the system to execute the acts of the method.

An object of the invention is achieved by a computer-readable medium having stored thereon the computer program.

A second object of the invention is achieved by a system for in-situ accumulation of sub-stances. The system comprises:

a frame arrangement supporting an actuator. The actuator is configured to drive a spindle defining a displacement axis. The spindle may be coupled to;

a flange for a displacement along the displacement axis. The flange may support a piston crown. The piston crown may be configured to operate in a chamber defining a chamber volume as a function of the piston crown. The chamber having means for being fixed to the frame arrangement, and being in a liquid connection with a cartridge with a sorbent.

The system may be placed in a liquid environment, such as a sea, a river, a tube with flowing liquid, a lake, a ground water reservoir or wetted soil.

When turning the spindle, the piston crown changes the chamber volume, and the change of the chamber volume enables driving a liquid volume through the sorbent when the cartridge is placed in a liquid environment.

Thereby, the system will drive a liquid volume equal to the change in chamber volume through the sorbent. The total liquid volume through the sorbent is the accumulated liquid volume, which will increase when repeatedly driving a liquid volume through the sorbent.

The change in the chamber volume is proportional to the rotation of the spindle. The rotation of the spindle causes the flange to be displaced along the displacement axis and thus the piston crown will be displaced along the displacement axis.

The piston crown defines an end of a piston. The piston crown may be supported to the flange by a piston shaft extending from the flange to the piston crown. The piston shaft may extend parallel to the displacement axis as this will cause the displacement of the flange to be equal to the displacement of the piston crown relative to the displacement axis. Thereby, the precision of the system increases as there is a direct correlation between the rotation of the spindle and the change in volume.

The piston may be secured to the flange by a piston foot adapted for engaging with the flange.

The piston foot may be secured by gluing the piston foot to the flange or by screwing a screw through the piston foot into the flange. Unwanted displacement of the piston and thus the piston crown is limited as a function of the connection between the piston and the flange.

In an embodiment, the piston foot is secured to the flange by two screws on each side of the piston flange, thereby limiting unwanted displacement and increasing the precision of the system.

Any displacement, which is not parallel to the displacement axis, decreases precision. In severe cases unwanted displacement may cause the liquid connection between the cartridge and the chamber to be broken.

The system may be arranged such that liquid is present on both sides of the flange relative to the displacement axis such that the flange is exposed to the same pressure and thus the same force on both sides of the flange. The effect is that the precision of the displacement of the flange increases significantly, which will result in more precise measurements.

The chamber may comprise a chamber channel adapted for displacement of the piston crown parallel to the displacement axis, while forming a liquid-tight connection with the piston crown such that liquid may only enter and exit the chamber through the liquid connection.

The piston crown may be equipped with one or more piston rings for increasing the liquid-tight connection between the liquid crown and the chamber, while having a sufficiently low friction such that the piston crown may be displaced.

The piston crown has two positions which define a minimum chamber volume and a maximum chamber volume. The chamber has its minimum chamber volume when a distance between the liquid connection and the piston crown is at a minimum.

The minimum chamber volume may be zero or close to zero because it is easier to control compared to having a minimum chamber volume different from zero. Thereby, drift of the change in volume is prevented or at least minimised which decreases the uncertainty which would otherwise increase significantly over several acts of driving a single liquid volume through the sorbent.

The chamber has its maximum chamber volume when the distance between the liquid connection and the piston crown is maximised while the piston crown is still firmly connected to the chamber. The skilled person would by trial and error be able to determine the maximum chamber volume for a specific system design or for specific chamber and piston designs.

The system may when placed in a liquid environment perform an act of driving a single liquid volume by displacing the piston crown in the chamber having an initial chamber volume, such that the volume of the chamber increases. The chamber is through the liquid connection with the cartridge connected to the liquid environment and the increase in volume will cause a negative pressure at the chamber relative to the liquid environment. The negative pressure is the driving force for driving liquid through the cartridge and the sorbent into the chamber until there is no pressure difference between the chamber and the liquid environment. This ensures that the volume of the liquid volume is equal to the change in volume of the chamber. The change in volume of the chamber can be controlled reliably and precisely.

Thus, the system removes or at least significantly decreases the drift in the size of liquid volume, thus the first liquid volume driven through the sorbent is equal to or at least almost equal to the 100th liquid volume driven through the sorbent.

The liquid in the chamber may afterwards be removed by resetting the piston crown, such that the chamber has the initial chamber volume. This will cause the liquid to be pushed out of the chamber and through the cartridge.

The initial chamber volume may be zero or close to zero.

The skilled person would realize that the system is only active and only consumes energy when displacing the piston crown. The system is passive while the liquid drives through the sorbent and into the chamber, thereby the system is energy efficient because the displacement of the flange and the piston crown is not energy demanding.

Thus, the system is able to repeatedly drive precise liquid volumes through the sorbent in an energy efficient manner.

The system may be hibernating while the chamber is filed with liquid for reducing idle power consumption.

The low energy consumption and reliable system enable accumulation of one or more substances over a time period of 0.5-2 months without service, which is not possible today. The system may perform 50-200 acts of driving a liquid volume through the sorbent over the period of 0.5-2 months.

The cartridge may comprise an inlet in direct contact with the liquid environment, when in intended use.

The cartridge may comprise an outlet connected to the liquid connection, wherein the sorbent is arranged between the inlet and the outlet.

In an embodiment, the sorbent may be positioned near the outlet for limiting the amount of residual liquid between the sorbent and the liquid connection.

Furthermore, if the sorbent is positioned near the inlet and the cartridge is placed in a river with a strong current, then the residual liquid may be dragged out through the sorbent by the current. This would cause a drop in pressure between the sorbent and liquid connection causing an uncontrolled movement of liquid through the sorbent, thereby the precision is lowered significantly.

The sorbent in the cartridge may be an adsorbent or an absorbent.

The sorbent may be adapted for accumulating a specific substance or a specific group of substances.

The sorbent may be adapted for accumulating nitrates, phosphates, oils, pesticides or pharmaceuticals. The sorbent may be adapted for accumulating other substances.

The sorbent may be a solid-phase extraction sorbent sold by companies, such as Waters or Merck.

The sorbent may be a different kind of sorbent sold by other or the same companies.

The sorbent may afterwards be removed from the system and analysed in a laboratory.

The chamber is fixed to the frame arrangement to ensure that the displacement of the flange causes the piston crown to be displaced in the chamber without any uncontrolled displacement of the chamber as this would cause a drift in the liquid volume, thereby causing the liquid volume to differ uncontrollably between each act of driving a liquid volume through the sorbent.

The chamber may be fixed by columns extending from the frame arrangement to chamber.

The frame arrangement may comprise a shell extending in the general direction of the spindle. The shell may at least partially surround the spindle, the flange, the chamber and the cartridge. The chamber may have means for being fixated to the shell.

In an embodiment, the shell surrounds the spindle, the flange, the chamber and the cartridge.

Both embodiments of the shell protect the mechanical parts of the system from fish, strong currents or objects moved by the currents.

The shell must not seal the system from the liquid environment and therefore the shell may have diffusion gaps for diffusion of the liquid in the liquid environment.

In an embodiment, the system is adapted for in-situ accumulation of substances in a fluid environment. Thereby, the use of the system is increased.

In an aspect of the invention, the system may comprise a chamber plate fixed to the frame arrangement. The chamber plate is adapted for fixating the chamber.

The chamber plate makes it easier to secure the chamber plate to the frame arrangement as the chamber plate can be secured at two or three or more points to the frame arrangement. Thereby, drift of the liquid volume is decreased and the system becomes more reliable.

The chamber plate may be fixed to the chamber by gluing or screws or a friction member.

The chamber plate may have a chamber aperture for insertion of the chamber.

The chamber aperture may have a friction member for fixating the chamber.

In an embodiment, the system may comprise a first chamber plate and a second chamber plate and the chamber comprises chamber wings, wherein the first chamber plate and the second chamber plate secure the chamber by clamping the chamber wings.

The first chamber plate and the second chamber plate may have two, three or more male connections for fixation with the shell having corresponding first and second chamber plate channels, each having a lock arrangement for limiting the movement of the chamber plates.

Tests have shown that this particular embodiment is mechanically stable over time and the embodiment also makes it easy to change the different mechanical components as there is no need for screwing or unscrewing.

In an aspect of the invention, that the system may comprise an end plate fixed to the frame arrangement. The end plate may have a spindle recess for receiving the spindle.

The spindle has a spindle end distal to the actuator. The spindle end will if not retained oscillate and the oscillation may above a certain length of the spindle be a problem. The skilled person would through experiments be able to determine the length of the spindle where this oscillation becomes a problem when driving precise liquid volumes. The oscillations of the distal spindle end can be minimised by inserting the spindle into the spindle recess. Thereby, the system becomes more stable because the movement of the spindle is controlled better, which causes any displacement of the piston crown to be controlled with a higher precision and thus the change in volume of the chamber is controlled with a higher precision.

Thereby, the system can take more precise liquid volumes and the system can repeatedly drive liquid volumes through the sorbent without a substantial drift in volume.

The end plate may comprise one or more shell recesses for connecting with the shell.

The shell recess may form a channel axial to the displacement axis for engaging with the shell, which may completely surround the recess, the channel, the cartridge and the flange.

In an aspect of the invention, the end plate constitutes at least 40%, 50%, 70%, 85% or 95% of a total weight of the system.

The large weight of the end plate relative to the entire system ensures that the end plate and the system can be positioned on the bottom of a sea, a pipe, a river or a lake without the risk of the system toppling.

The weight of the end plate must increase relative to the whole system with increasing liquid flow in the liquid environment for the system to remain stable.

The frame arrangement supports the actuator and the battery in a section which is sealed from the liquid environment. The section is lifted by the fluid environment due to buoyancy. The end plate and actuator are positioned distal to each other and thus both the lift on the section with the actuator and the battery, and the weight of the end plate work together to stabilise the system when in the liquid environment.

In an embodiment, the system is floating in the liquid environment due to buoyancy of the system, wherein the end plate is anchored to a bottom of the liquid environment. The frame arrangement is connected to a buoy at a top of the liquid environment.

In an aspect of the invention, that the flange may comprise two or more indents at a periphery of the flange. The two or more indents may be adapted for interacting with two or more rods extending substantially parallel to the displacement axis and being supported longitudinally along part of the frame arrangement.

A non-uniform force may affect the flange causing the flange to flex or twist. The indents at the periphery of the flange and the rods which are positioned in the indents will reduce the flexing and/or twisting of the flange when the flange is affected by a non-uniform force. The force interaction between the flange and the rods can be very large and therefore the rods are supported longitudinally along part of the frame arrangement.

The rods and indents on the periphery of the flange stabilise the flange when the flange is being displaced parallel to the displacement axis, and thus any twisting or flexing due to friction forces between different components, such as piston crown and chamber, is avoided. This causes the system to be able to drive well-defined liquid volumes through the sorbent with a high reproducibility as the volume drift is minimised.

In an embodiment, the rods are secured to the shell by gluing.

In another embodiment the shell is made having two or more rods integrated into the shell as this will increase the overall strength.

In an embodiment the periphery of the flange and the shell has complementary shapes such that the parts of the shell without rods also contribute to keeping the flange stable.

In an embodiment, the periphery of the flange is substantially circular and the shell is substantially a hollow circular cylinder as this is a simple and reliable design.

In an aspect of the invention, the end plate comprises two or more bores for insertion of and supporting part of the rods. The extra supporting of the rods make the system more reliable as the rods are better secured.

In an aspect of the invention, the liquid connection may comprise an exhaust adapted for expelling fluid from the chamber. This will reduce the amount of liquid expelled back through the cartridge and sorbent and the pressure on the sorbent is decreased reducing the risk of the sorbent being pushed out of the cartridge when expelling liquid from the chamber.

The exhaust may be equipped with a one-way exhaust valve, such that liquid does not enter the chamber when there is a negative pressure in the chamber relative to the liquid environment, thus increasing the precision of the fluid volume passing the sorbent.

The liquid connection may further be provided with a one-way cartridge valve, such that when expelling liquid from the chamber, then the liquid is only expelled through the exhaust.

In an embodiment, the liquid connection may comprise an exhaust with a one-way exhaust valve, such that liquid does not enter the chamber when there is a negative pressure in the chamber relative to the liquid environment, and the liquid connection may also comprise a one-way cartridge valve, such that when expelling liquid from the chamber then the liquid is only expelled through the exhaust.

In an aspect of the invention, the system may comprise a cartridge plate fixed to the frame arrangement. The cartridge plate is adapted for stabilising the cartridge.

The cartridge plate does not need to fixate the cartridge but only stabilise the cartridge as the cartridge is connected to liquid connection. The cartridge may oscillate which may cause the cartridge and liquid connection to disconnect.

The cartridge plate may have cartridge plate apertures for limiting the oscillation of the cartridge.

The cartridge plate may relative to the displacement axis be slightly displaced from the inlet of the cartridge such that the cartridge plate interacts with the part of the cartridge having the largest amplitude.

The cartridge plate may be fixated to the frame arrangement by columns extending from the frame arrangement.

In an embodiment, the cartridge plate is fixated to the shell.

In an embodiment, the cartridge plate comprises two, three or more male connections for interacting with the shell. The shell may comprise a cartridge plate channel adapted for receiving the male connections.

In an embodiment, the cartridge plate is circular and the shell is a circular hollow cylinder complementary to the cartridge plate.

In an aspect of the invention, the system may comprise two or more piston crowns and two or more corresponding chambers defining two or more chamber volumes, and two or more cartridges.

The two or more cartridges are connected to the two or more chambers by two or more liquid connections and the two or more cartridges comprising two or more sorbents.

Thereby, the system may simultaneously drive two or more fluid volumes trough two or more sorbents.

The two or more sorbents may be identical and the cartridges may be sent to two different laboratories for determining the accumulation of substances.

The two or more sorbents may measure the same substance or substance group and the cartridges may be sent to the same or different laboratories for determining the accumulation of the substance or substance group.

The two or more sorbents may measure different substances or substance groups and the cartridges may be sent to the same or different laboratories for determining the accumulation of the substance or substance group.

In an aspect of the invention, that the system may comprise two or more piston crowns and two or more corresponding chambers defining two or more chamber volumes, and two or more cartridges, wherein the piston crowns, the chambers and the cartridges are positioned symmetrically relative to the displacement axis.

The force on the flange will be distributed evenly when positioning the piston crowns, the chambers and the cartridges are positioned symmetrically relative to the displacement axis. Thereby the flange to moves precisely with little to no twisting or flexing, when comparing the system to a system having only a single piston crown, a single chamber and a single cartridge.

The two or more cartridges are connected to the two or more chambers by two or more liquid connections and the two or more cartridges comprising two or more sorbents.

In an aspect of the invention, the system may comprise two or more piston crowns and corresponding two or more chambers defining two or more chamber volumes as two or more functions of the two or more the piston crowns, and two or more cartridges, wherein the piston crowns, the chambers, and the cartridges are arranged to establish force symmetry relative to the displacement axis.

The two or more chambers and corresponding two or more the piston crowns may define two or more chamber volumes, which may be defined from two different functions of the displacement of the piston crowns. Thus, two chambers having piston crowns with the same displacement may have two different chamber volumes. This will cause a difference in the negative pressure in each chamber relative to the fluid environment and the flange will therefore experience two different forces. This difference may be mitigated by arranging the piston crowns, the chambers, and the cartridge to established force symmetry. Thereby, the system is enabled to drive different liquid volumes through the sorbents without compromising the reproducibility of each act of driving liquid volumes through the sorbents.

The two or more cartridges are connected to the two or more chambers by two or more liquid connections and the two or more cartridges comprising two or more sorbents.

In an aspect of the invention, the spindle may be connected to the flange by a ball screw. The ball screw will reduce slackness between the spindle and the flange. This will increase the precision of the displacement of the flange and this is important when performing 50-200 measurements without service.

In an aspect of the invention, the flange may comprise a neck extending perpendicularly from the flange towards the actuator. The neck comprises an internal thread adapted to engage with an end of the spindle.

There is a correlation between the length of the neck and the precision of the flange movement.

The neck may be the only stabilising part.

In an embodiment, the neck will be close to the frame arrangement when the chamber has the maximum chamber volume.

The system may comprise a battery for powering the actuator, such that the system may be a single unit.

The system may comprise a controller for controlling the entire system.

DESCRIPTION OF THE DRAWING

Embodiments of the invention will be described in the figures, whereon.

Figure 7:
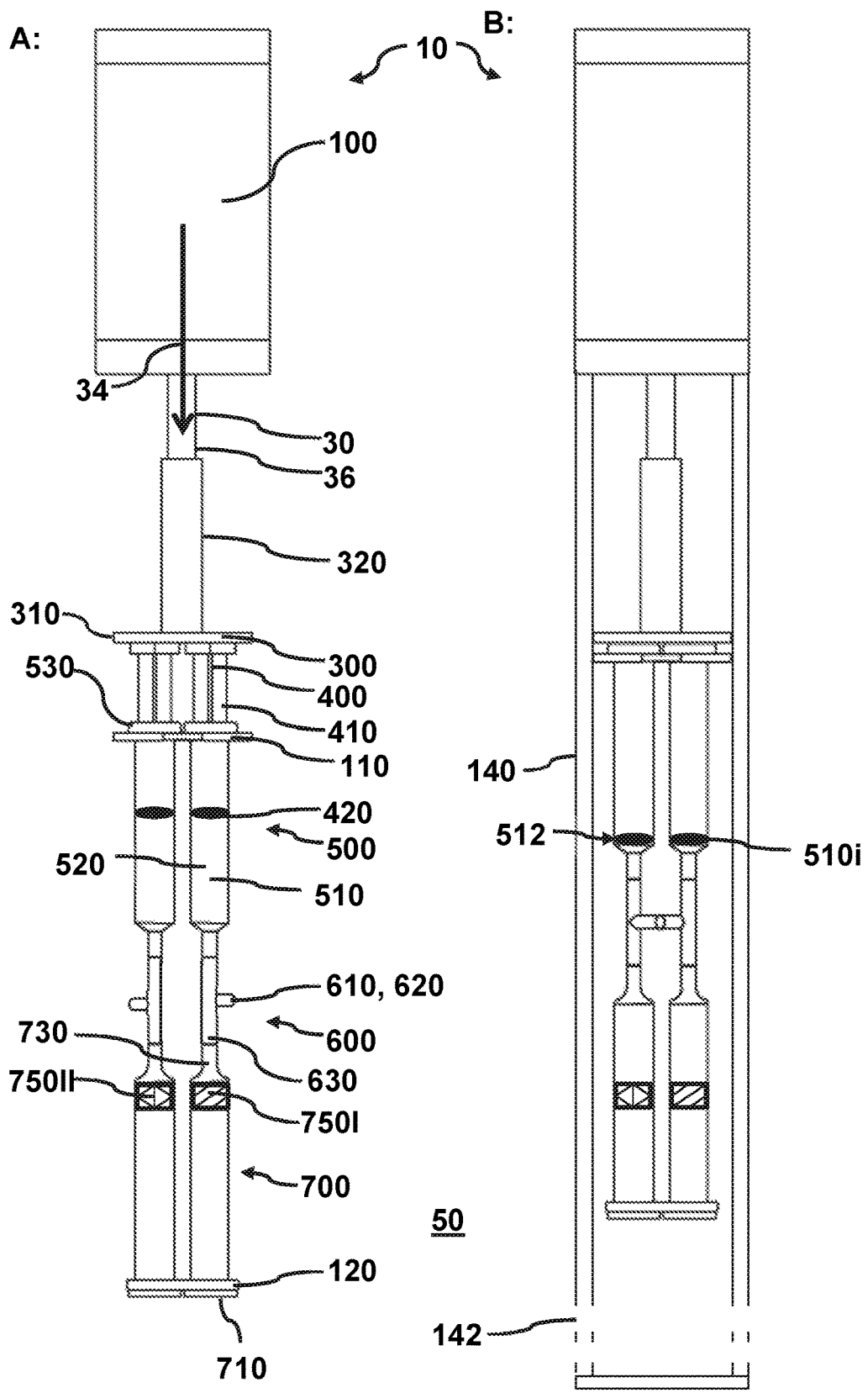
Figure 8:
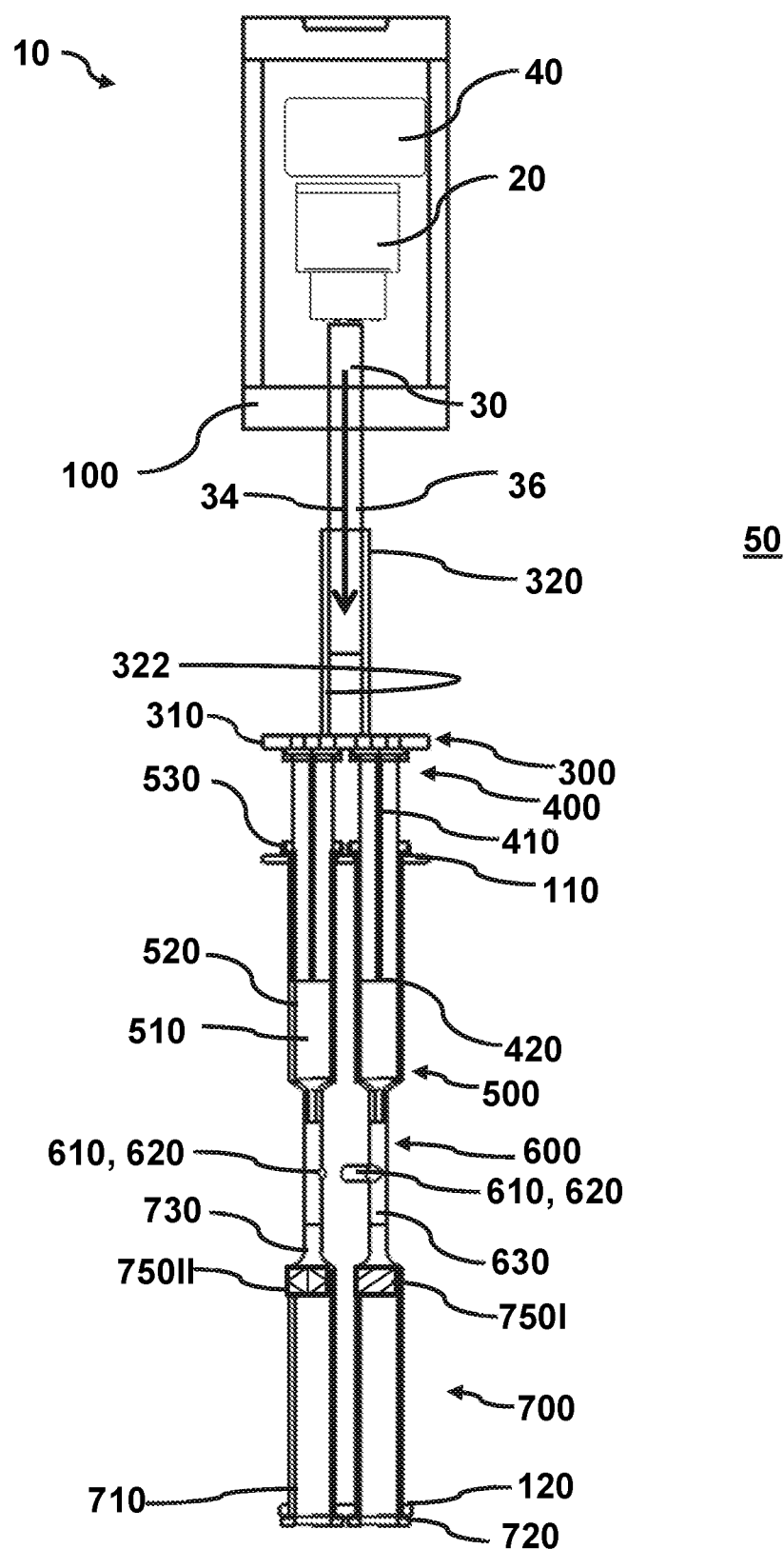
Figure 9:
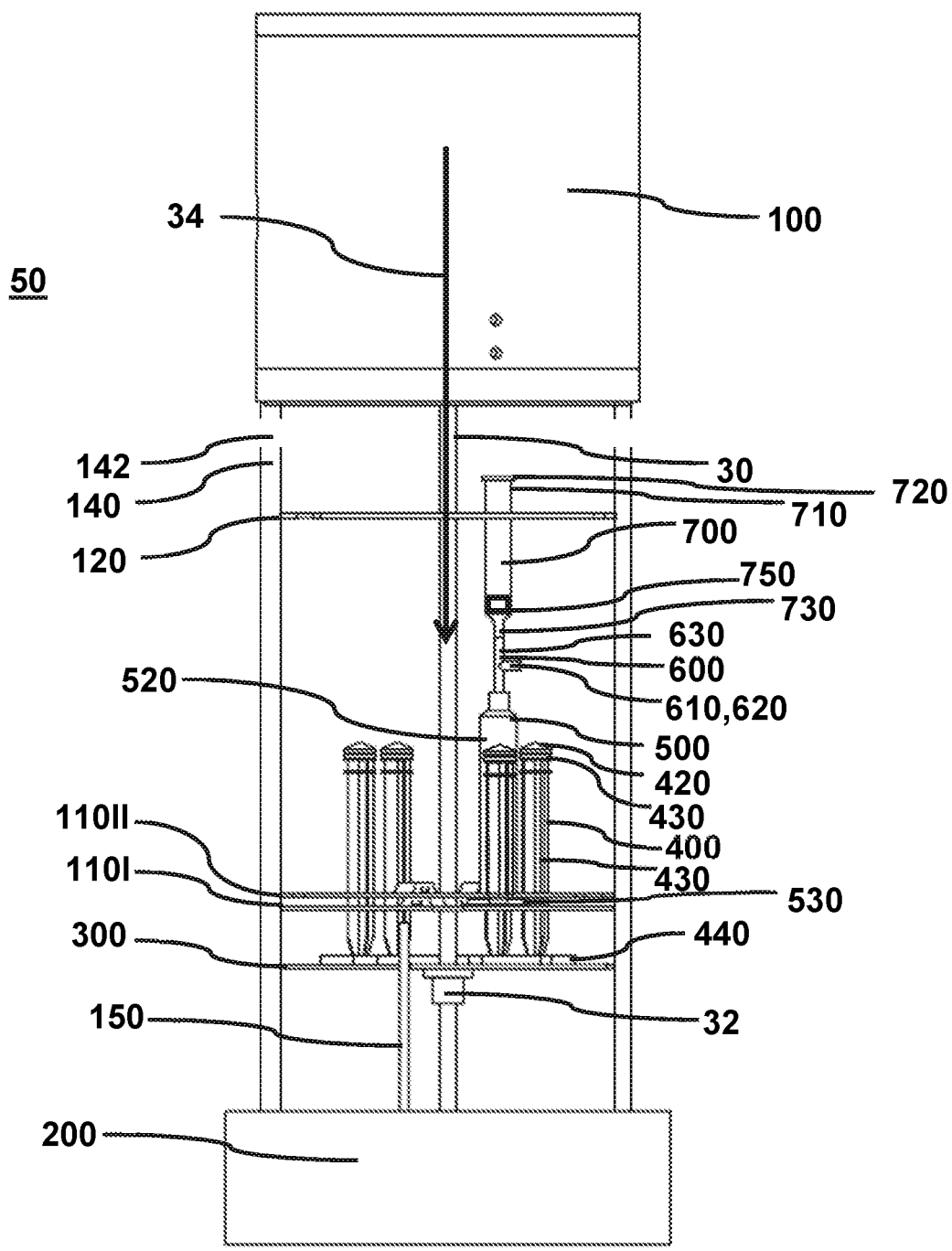
Figure 10:
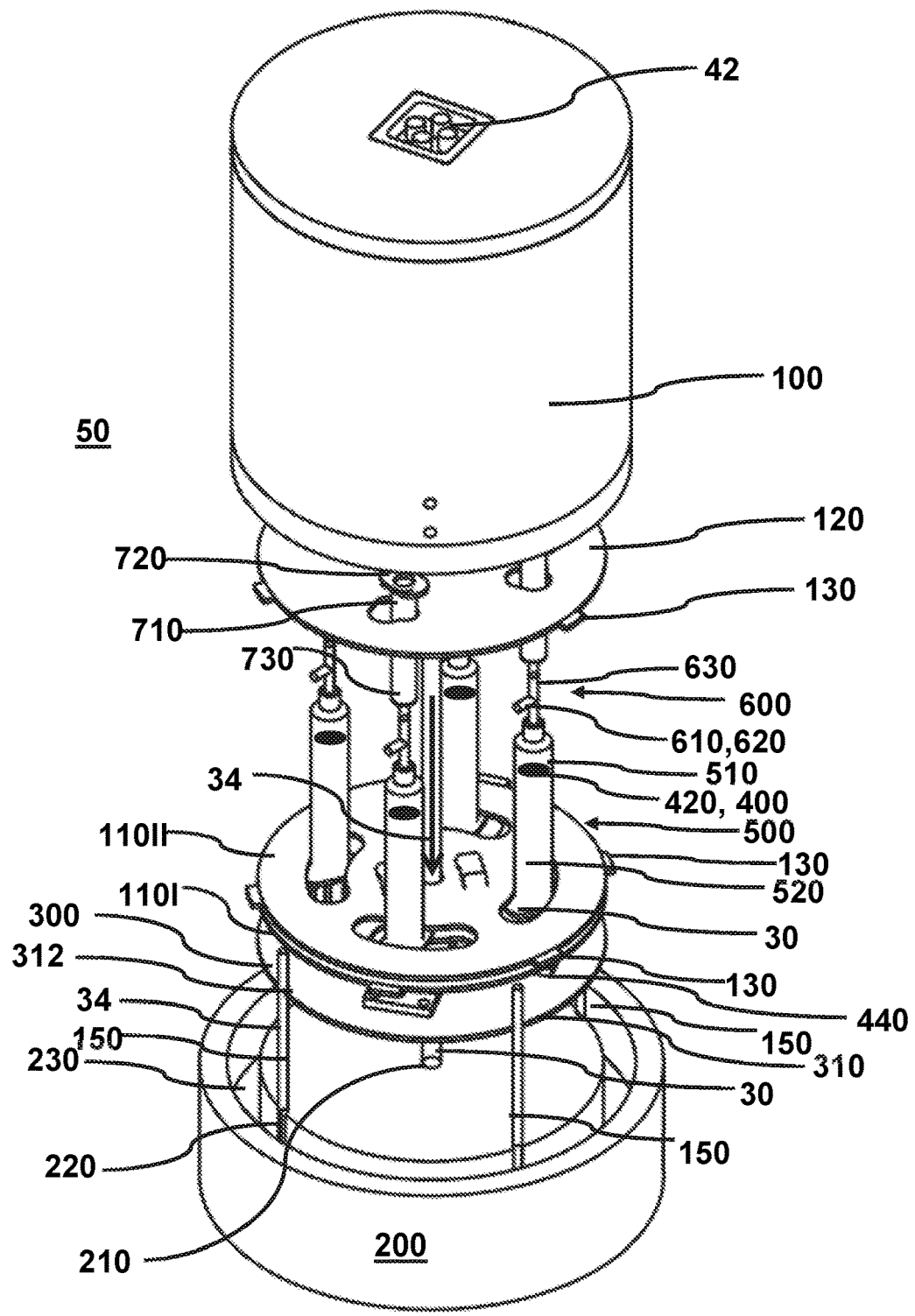
Figure 11:
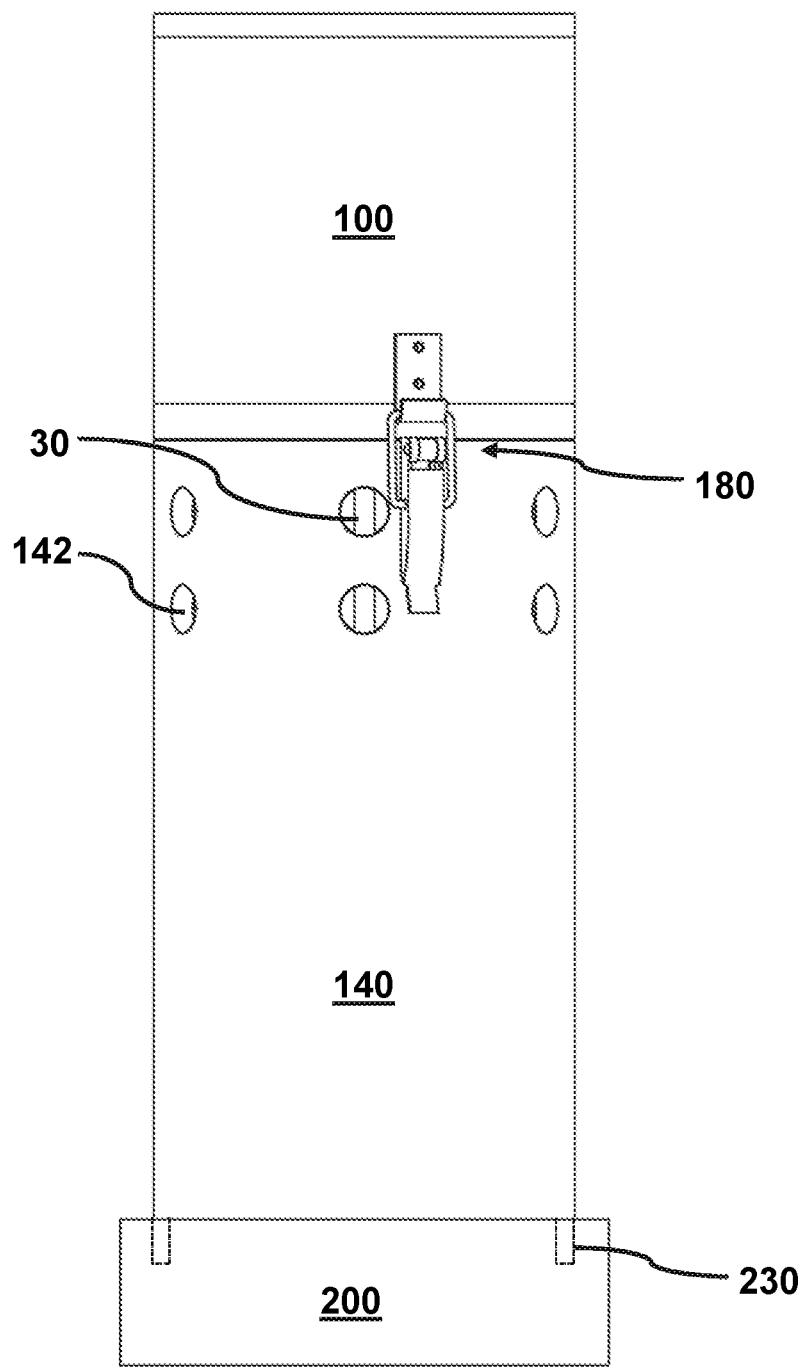
Figure 12:
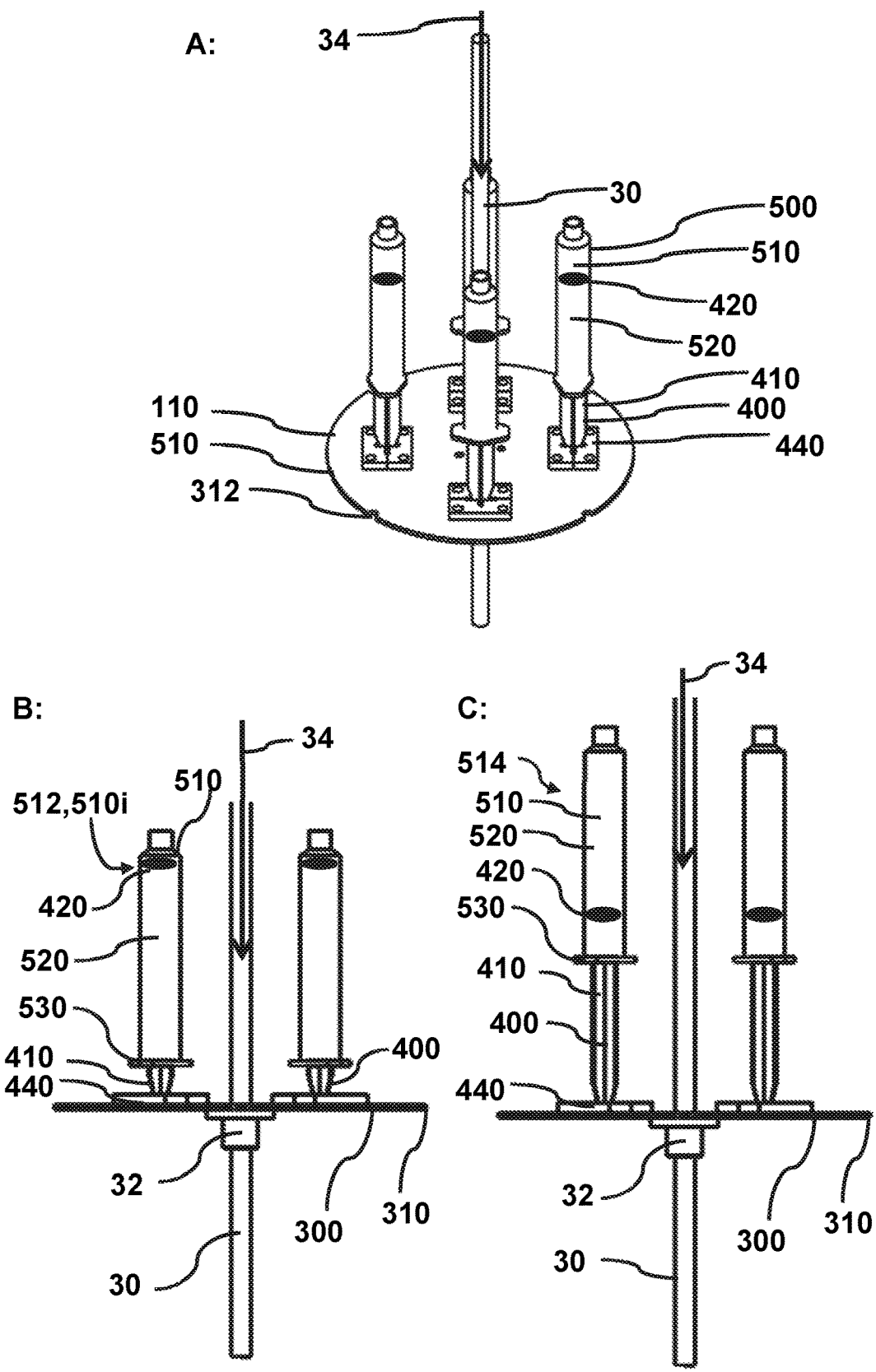
Figure 13:
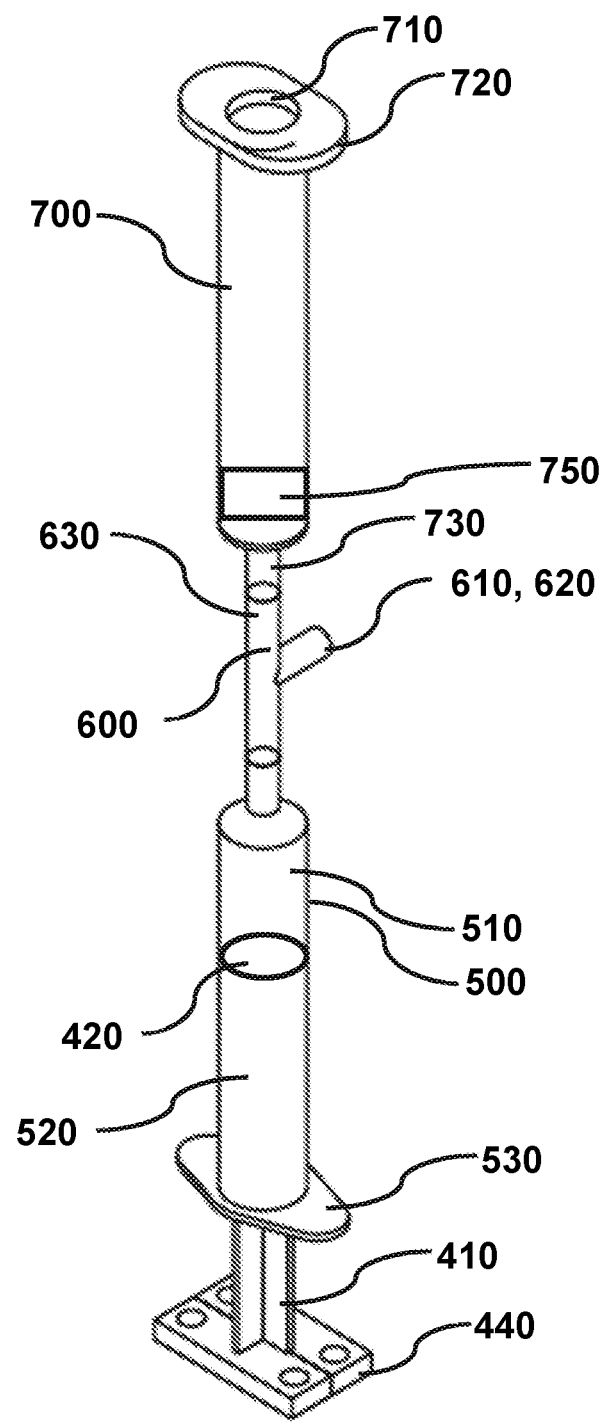
Figure 14:
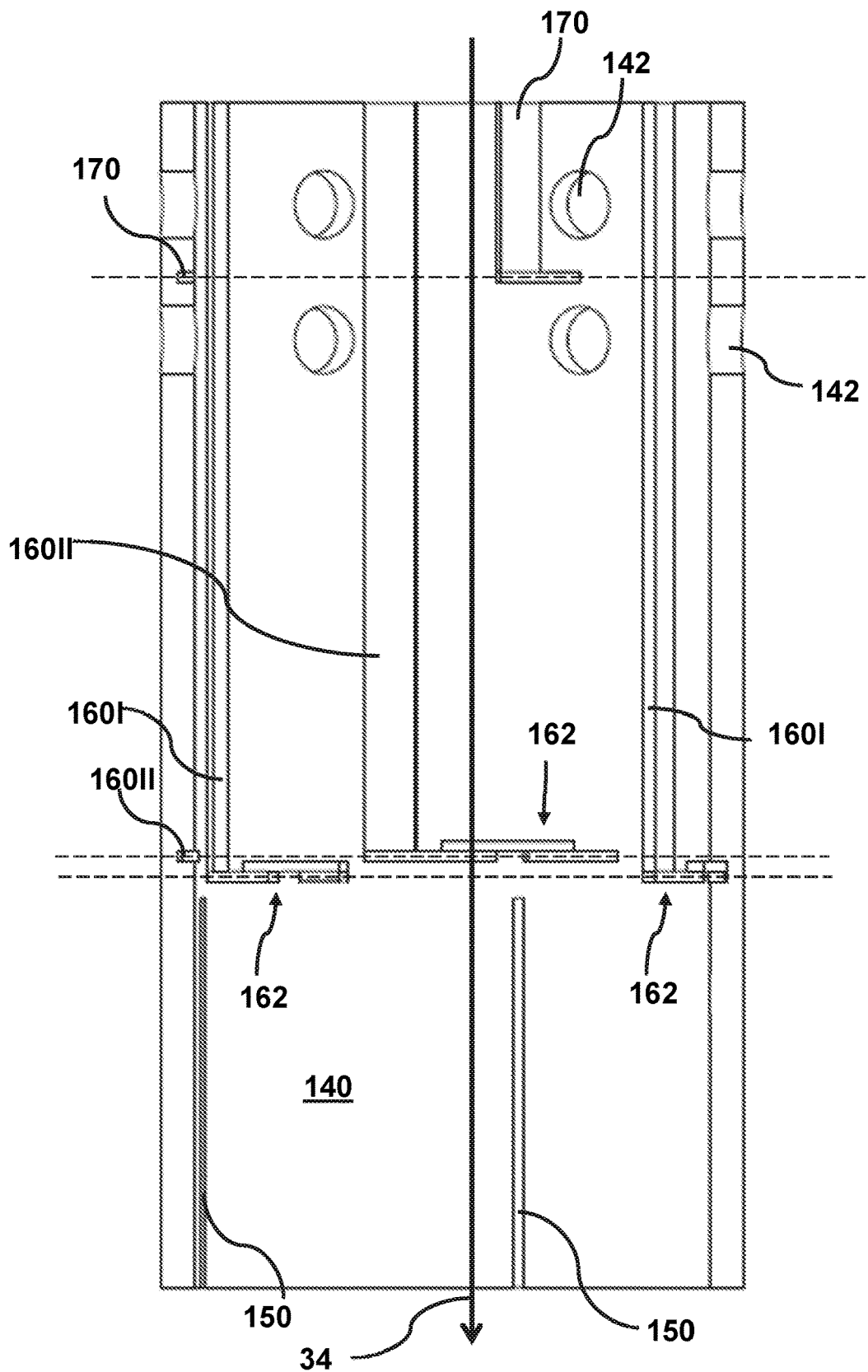
Figure 15:
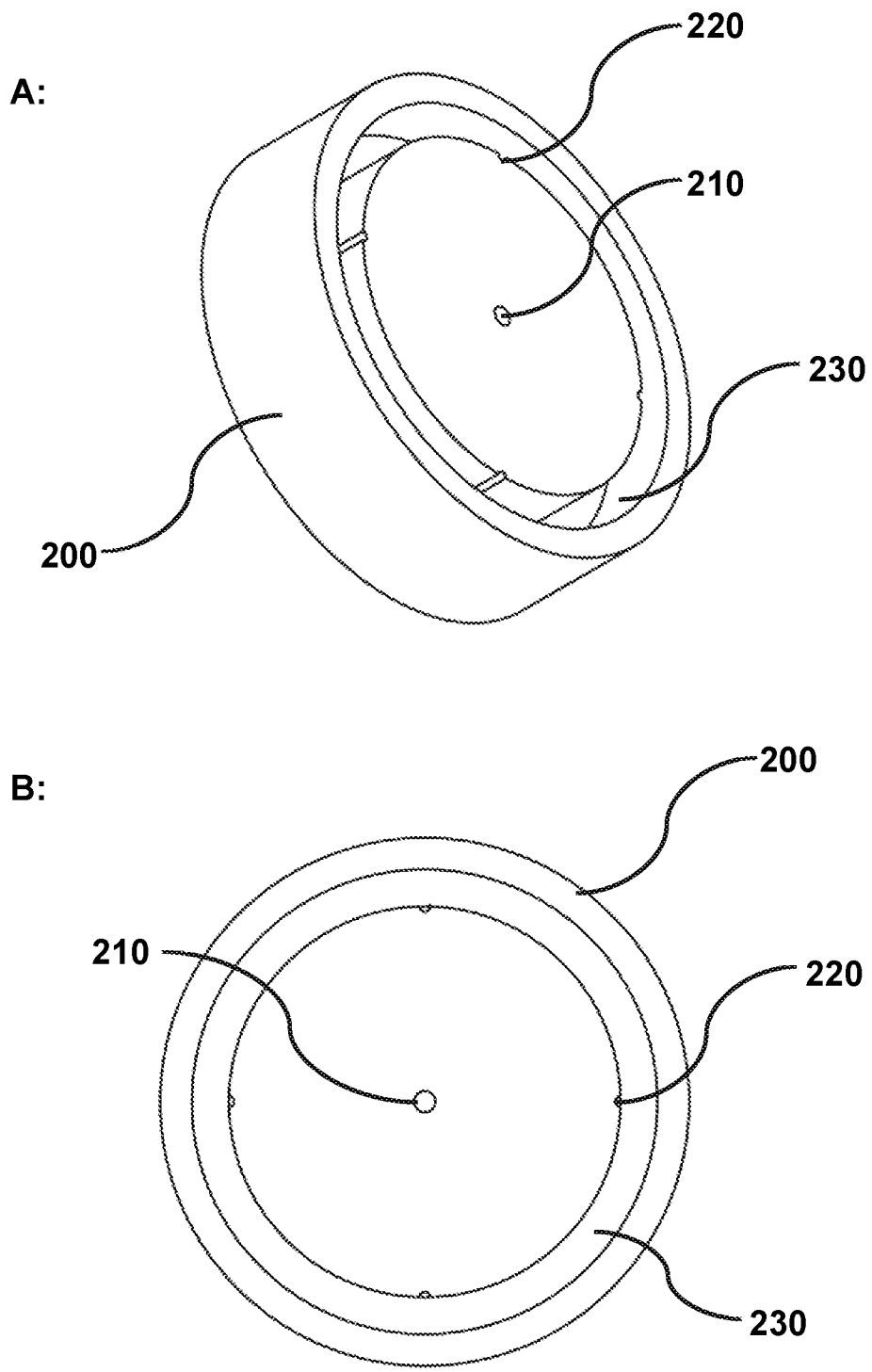
Figure 16:
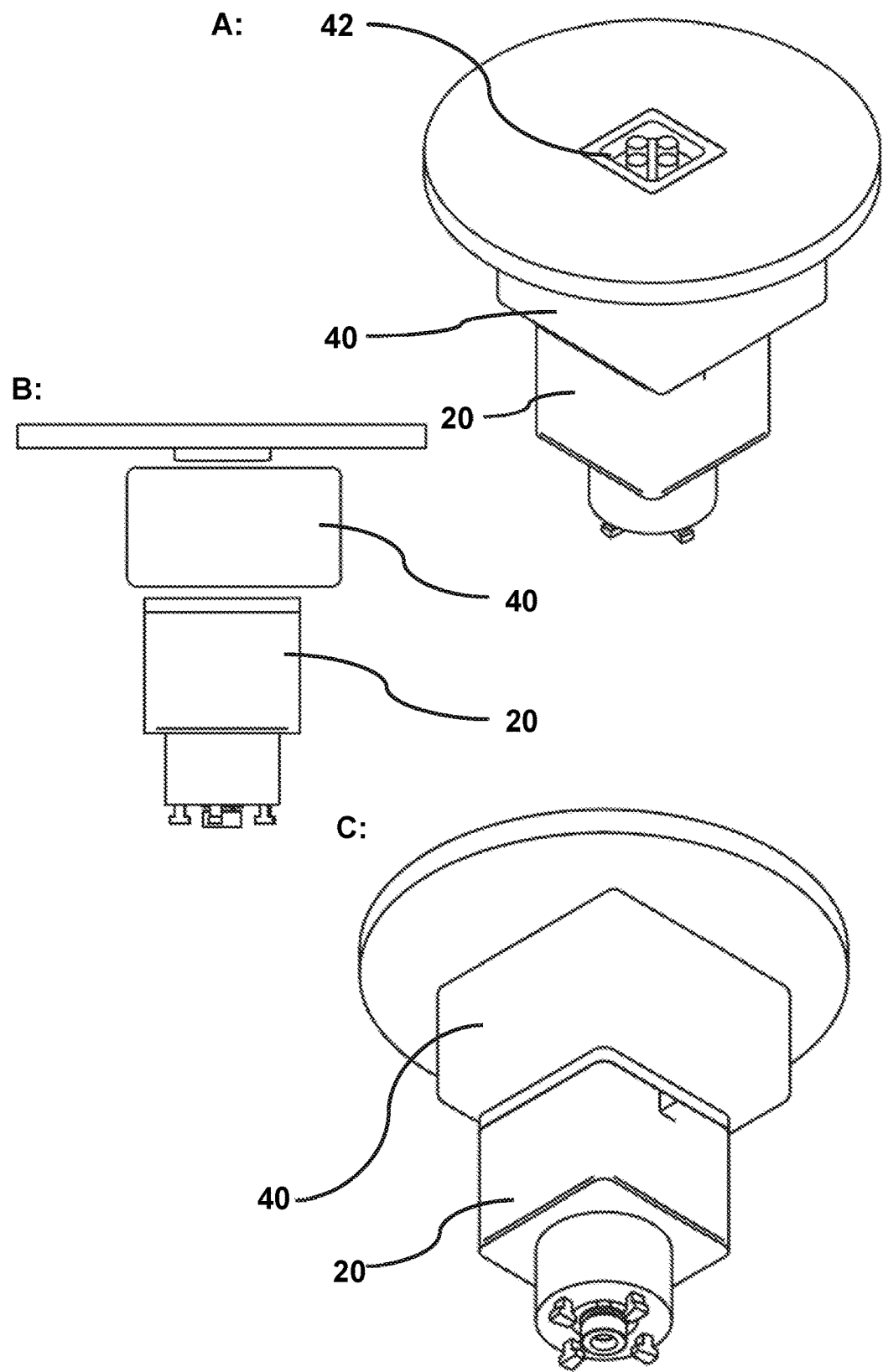
Figure 17:
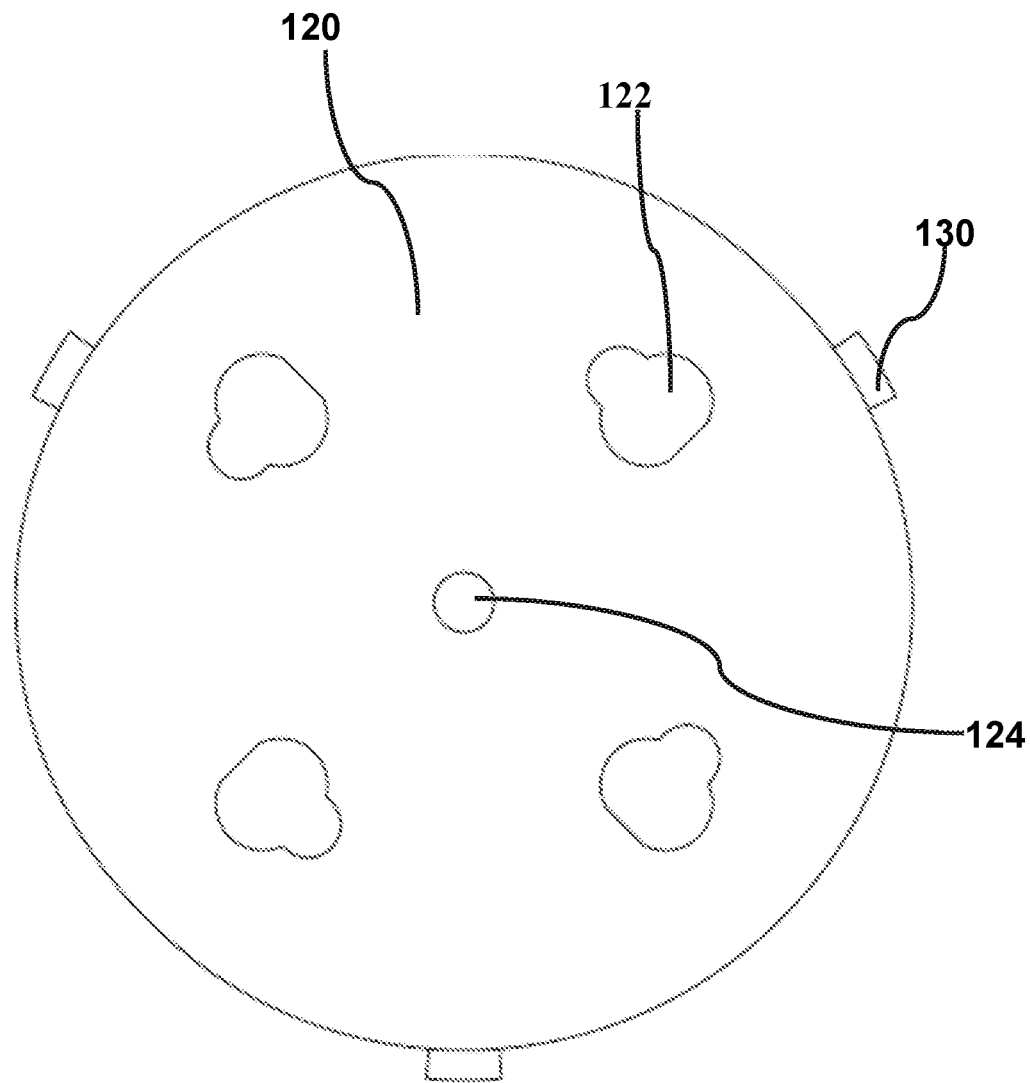
Figure 18:
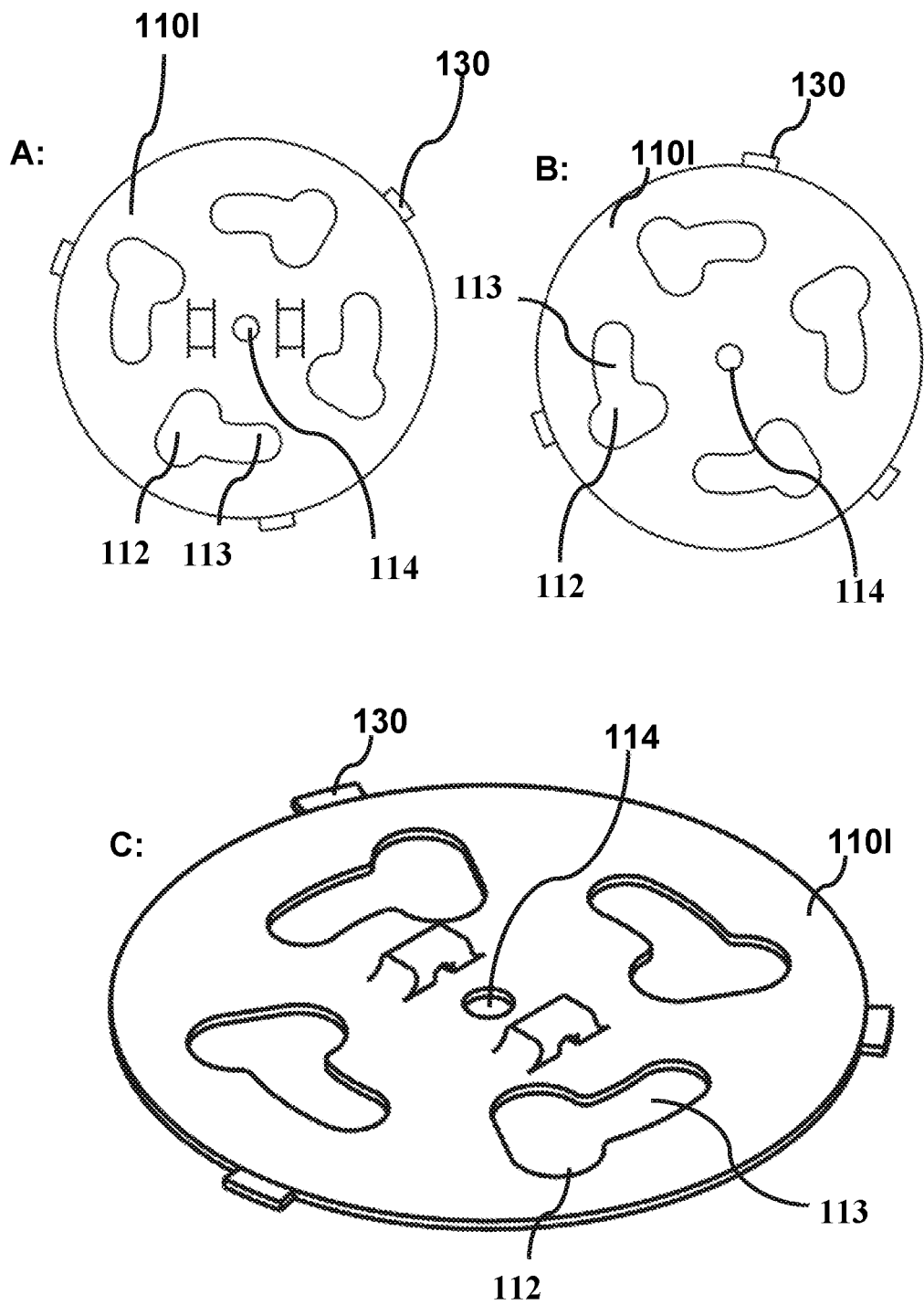

Embodiments of the second invention will be described in the figures, whereon:

FIG. 7 illustrates an embodiment of a system for in-situ accumulation of substances;

FIG. 8 illustrates a cross section of an embodiment of a system for in-situ accumulation of substances;

FIG. 9 illustrates a system for in-situ accumulation of substances;

FIG. 10 illustrates a top side view of a system for in-situ accumulation of substances;

FIG. 11 illustrates a system for in-situ accumulation of substances;

FIG. 12 illustrates a spindle with a flange supporting four pistons connected to chambers;

FIG. 13 illustrates setup of a piston, a chamber, a liquid connection and a cartridge;

FIG. 14 illustrates a cross section of a shell;

FIG. 15 illustrates end plate;

FIG. 16 illustrates an actuator and battery;

FIG. 17 illustrates a cartridge plate;

FIG. 18 illustrates a first chamber plate; and

Figure 19:
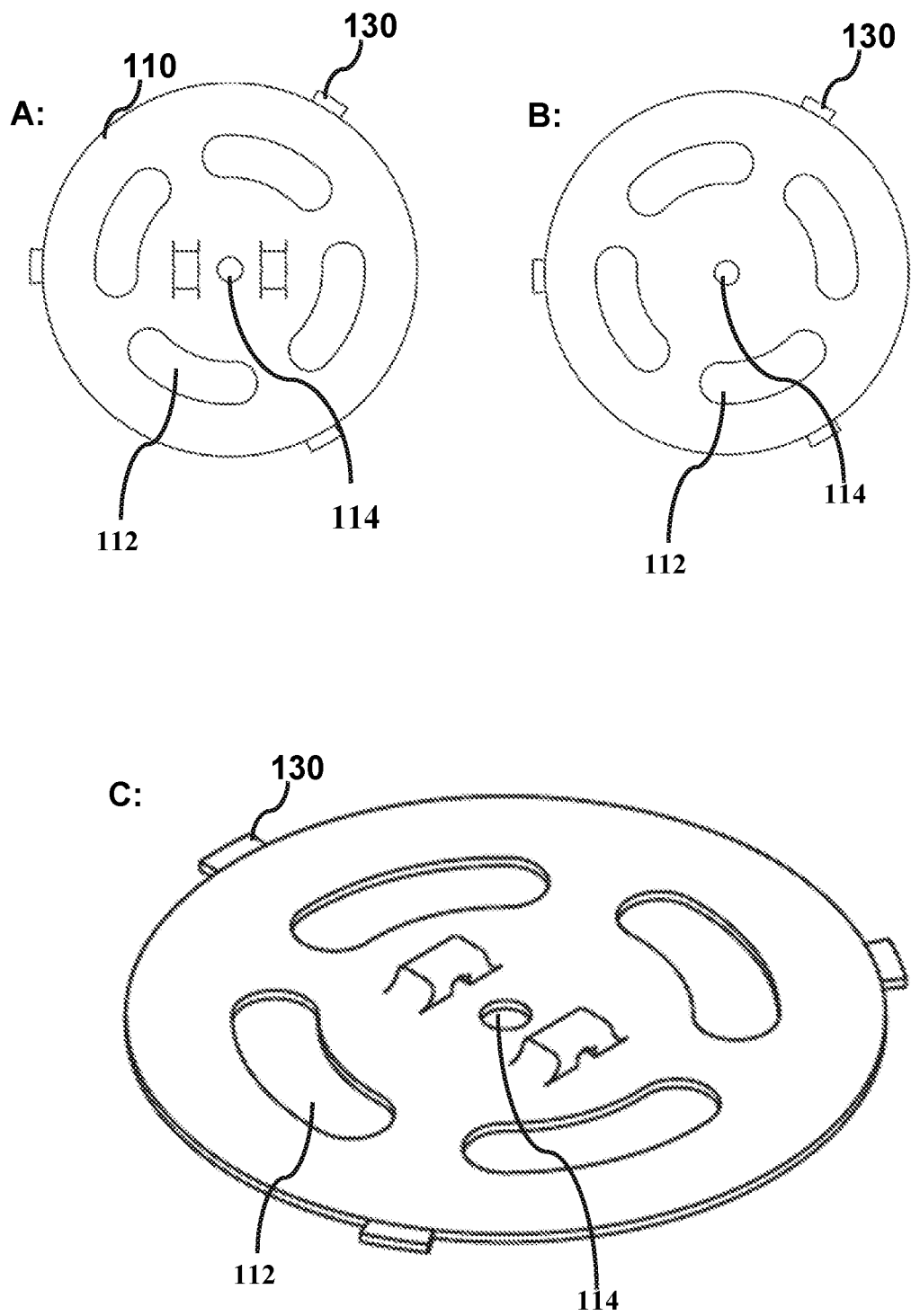

FIG. 19 illustrates a second chamber plate.

DETAILED DESCRIPTION OF THE INVENTION

| Item | No |
|---|---|
| System | 10 |
| Actuator | 20 |

-continued

| Item | No |
|---|---|
| Spindle | 30 |
| Ball screw | 32 |
| Displacement axis | 34 |
| External thread | 36 |
| Battery | 40 |
| Plug | 42 |
| Liquid environment | 50 |
| Frame arrangement | 100 |
| Chamber plate | 110, 110I, 110II |
| Chamber plate aperture | 112 |
| Chamber plate aperture recess | 113 |
| Chamber plate spindle bore | 114 |
| Cartridge plate | 120 |
| Cartridge plate aperture | 122 |
| Cartridge plate spindle bore | 124 |
| Male connection | 130 |
| Shell | 140 |
| Diffusion gap | 142 |
| Rod | 150 |
| Chamber plate channel | 160 |
| Lock arrangement | 162 |
| Cartridge plate channel | 170 |
| Clamp | 180 |
| End plate | 200 |
| Spindle recess | 210 |
| Bore | 220 |
| Shell recess | 230 |
| Flange | 300 |
| Periphery | 310 |
| Indents | 312 |
| Neck | 320 |
| Internal tread | 322 |
| Piston | 400 |
| Piston shaft | 410 |
| Piston crown | 420 |
| Piston ring | 430 |
| Piston feet | 440 |
| Chamber | 500 |
| Chamber volume | 510 |
| Initial chamber volume | 510i |
| Minimum chamber volume | 512 |
| Maximum chamber volume | 514 |
| Chamber channel | 520 |
| Chamber wing | 530 |
| Liquid connection | 600 |
| Exhaust | 610 |
| Exhaust valve | 620 |
| Cartridge valve | 630 |
| Cartridge | 700 |
| Cartridge inlet | 710 |
| Inlet wing | 720 |
| Cartridge outlet | 730 |
| Sorbent | 750 |
| Method | 1000 |
| Placing | 1100 |
| Driving | 1200 |
| Resetting | 1250 |
| Repeating | 1300 |
| Hibernating | 1350 |

Figure 1:
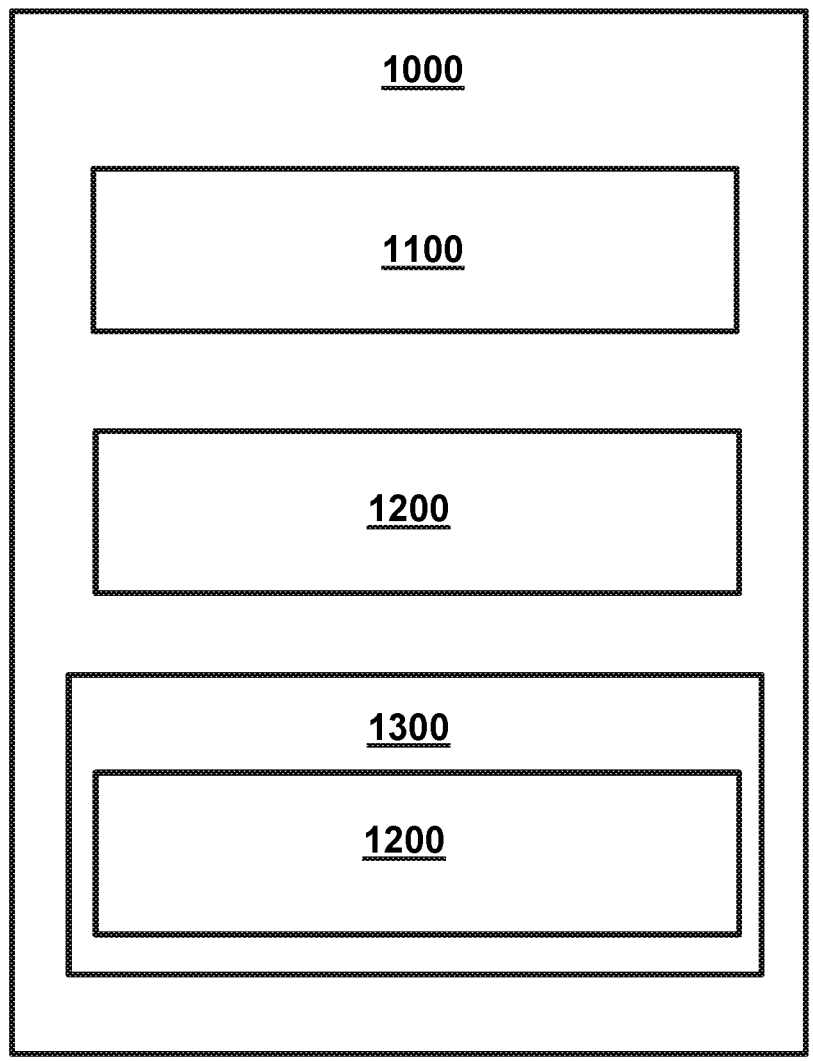
FIG. 1 illustrates a method for in-situ accumulation of one or more substances from a liquid environment.

FIG. 1 illustrates a method 1000 for in-situ accumulation of one or more substances from a liquid environment 50.

The method 1000 has an act of placing 1100 a cartridge 700 with a sorbent 750 in the liquid environment 50. The cartridge 700 can be placed in a river, a sea, a lake, a drilled bore in soil, ground water or any other kind of liquid environment 50.

The method 1000 has a further act of driving 1200 a liquid volume through the sorbent 750.

The sorbent 750 is designed for adsorbing or absorbing certain substances or substance groups. If the liquid volume contains one or more of the certain substances or substance groups, then these substances or substance groups will be adsorbed or absorbed by the sorbent 750.

The method 1000 has a further act of repeating 1300 the act of driving 1200 as a function of time.

The sorbent 750 will accumulate substances or substance groups during each act of driving 1200 provided that these substances or substance groups are present in the liquid environment 50. Because the number of acts of driving 1200 is known then the total liquid volume through the sorbent 750 is known. The sorbent 750 is afterwards tested for the total accumulation of the substances or the substance groups and from this one can determine whether the amount of substances or substance groups in the total liquid volume was above or below a threshold value.

The function of time may cause the act of repeating 1300 the act of driving 1200 one or more times between 4 PM and 8 AM the next day.

The function of time may cause the act of repeating 1300 the act of driving 1200 one or more times per day.

The function of time may randomly cause the act of repeating 1300 the act of driving 1200.

Figure 2:
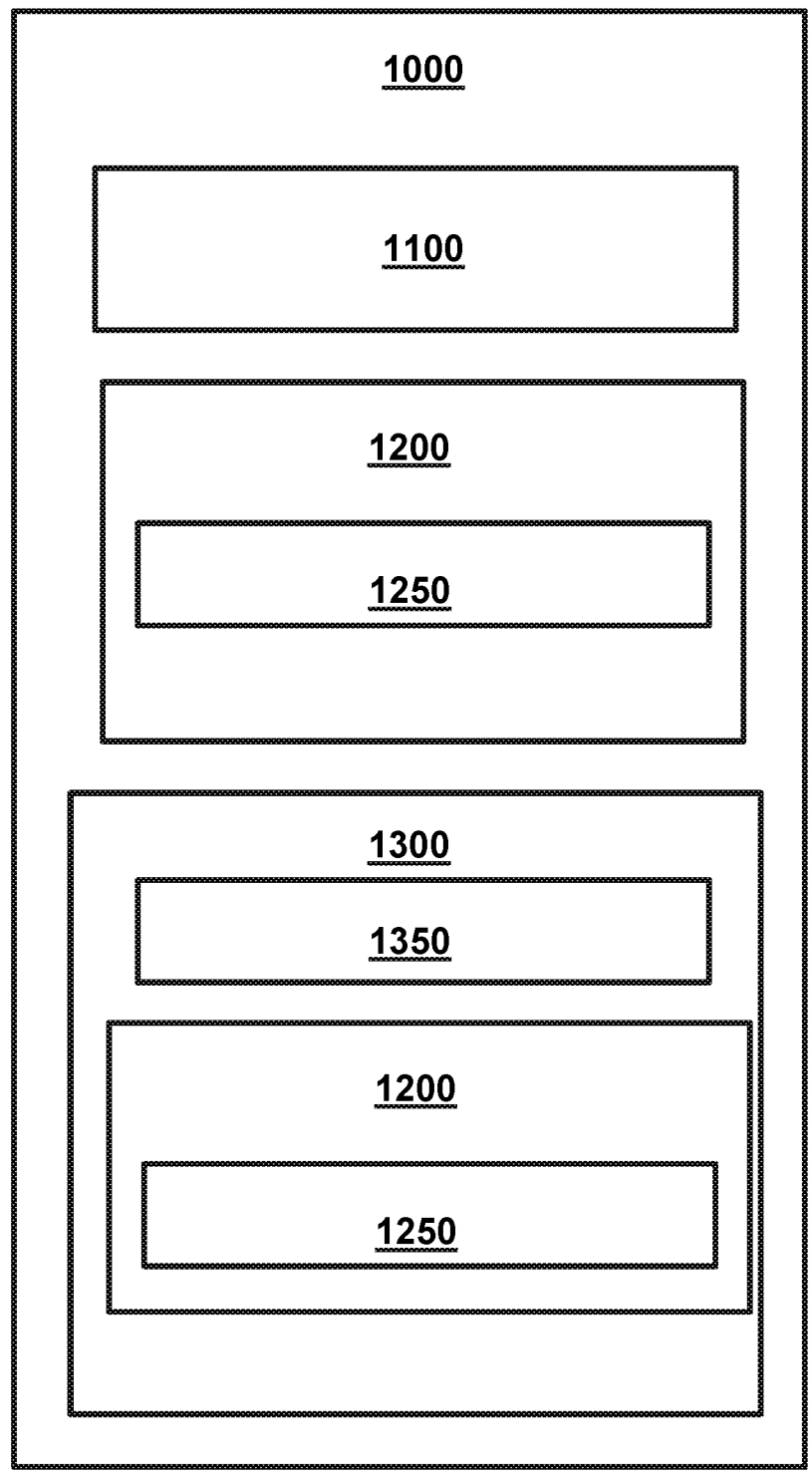
FIG. 2 illustrates another embodiment of a method for in-situ accumulation of one or more substances from a liquid environment.

FIG. 2 illustrates another embodiment of a method 1000 for in-situ accumulation of one or more substances from a liquid environment 50.

The method 1000 has an act of placing 1100 a cartridge 700 with a sorbent 750 in the liquid environment 50. The cartridge 700 can be placed in a river, a sea, a lake, a drilled bore in soil, ground water or any other kind of liquid environment 50.

The method 1000 has a further act of driving 1200 a liquid volume through the sorbent 750, wherein the act of driving 1200 is performed by changing a volume of a chamber 500 having an initial chamber volume 510i in liquid connection 600 with the cartridge 700.

The sorbent 750 is designed for adsorbing or absorbing certain substances or substance groups. If the liquid volume contains one or more of the certain substances or substance groups, then these substances or substance groups will be adsorbed or absorbed by the sorbent 750.

The act of driving 1200 includes an act of resetting 1250 the chamber 500 to the initial chamber volume 510i. Thereby, the chamber 500 can be smaller and it is easier control the chamber volume 510, when the chamber volume 510 does not have to increase with each act of driving 1200.

The method 1000 has a further act of repeating 1300 the act of driving 1200 as a function of time.

The sorbent 750 will accumulate substances or substance groups during each act of driving 1200 provided that these substances or substance groups are present in the liquid environment 50. Because the number of acts of driving 1200 is known then the total liquid volume through the sorbent 750 is known. The sorbent 750 is afterwards tested for the total accumulation of the substances or the substance groups and from this one can determine whether the amount of substances or substance groups in the total liquid volume was above or below a threshold value.

The function of time may cause the act of repeating 1300 the act of driving 1200 one or more time between 4 PM and 8 AM the next day.

The function of time may cause the act of repeating 1300 the act of driving 1200 one or more times per day.

The function of time may randomly cause the act of repeating 1300 the act of driving 1200.

The act of repeating 1300 includes an act of hibernating 1350 as a function of time between the acts of driving 1200. The act of hibernating 1350 makes the method 1000 more energy-efficient.

Figure 3:
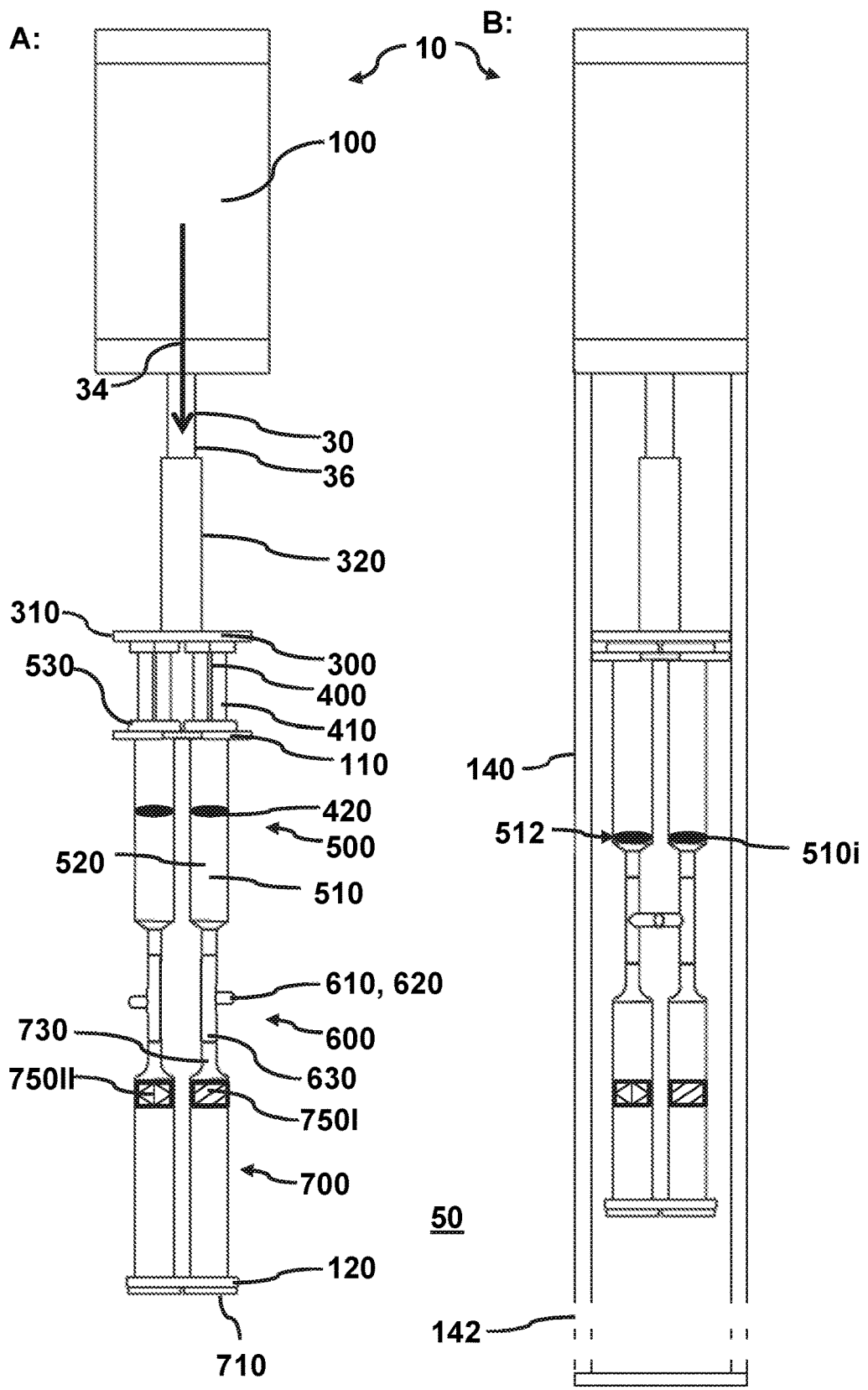
FIG. 3 illustrates an embodiment of a system for in-situ accumulation of substances.

FIG. 3 illustrates an embodiment of a system 10 for in-situ accumulation of substances.

FIG. 3A discloses the system 10 without a shell 140 and FIG. 3B discloses the same system 10 with a cross-section of a shell 140.

The system 10 has a frame arrangement 100 supporting a not shown actuator 20. The actuator is configured for driving the spindle 30. The spindle 30 defines a displacement axis 34 which extends in the same direction as the spindle 30.

An end of the spindle 30 is connected to a flange 300, the flange 300 has a neck 320 extending towards the not shown actuator 20. The neck 320 has a not shown internal thread 322 for engaging with an external thread 36 of the spindle 30. The neck 320 which has a substantial length ensures that the displacement of the flange 300 is precise with little to no twisting or flexing.

The flange 300 has a flange periphery 310 defining a shape complementary to the shell 140.

The flange 300 supports two pistons 400, each piston 400 being connected to the flange 300 by the piston foot 440 which is secured to the flange 300 using screws. Each piston 400 has a piston shaft 410 extending from the piston foot 440 to the piston crown 420.

Each piston crown 420 being configured to operate in a chamber 500. The complementary piston crowns 420 and chambers 500 define a chamber volume 510 as a function of the displacement of the piston crown 420. In FIG. 1B, the chamber volume is at a minimum chamber volume 512 which will typically be the initial chamber volume 510$i$.

Each chamber 500 has a chamber wing 530 which is used to fixate the chamber 500 to a chamber plate 110. The chamber plate 110 is in FIG. 3B connected to the shell 140 and thereby the chamber 500 is secured relative to the frame arrangement 100.

Each chamber 500 has a chamber channel 520 adapted for displacement of the piston crown 420.

The chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600, an inlet 710 in direct contact with liquid environment 50 when in intended use.

The cartridges 700 have two different sorbents 750I, 750II for accumulation of two different substances or two different substance groups.

The cartridges 700 are stabilised by a cartridge plate 120 fixed to the frame arrangement 100 by the shell 140.

The shell 140 has diffusion gaps 142 for diffusion of liquid from the liquid environment 50 into the system 10.

The system 10 will accumulate substances by actuating the spindle 30 causing the flange 300 to be displaced parallel to the displacement axis 34. The piston crowns 420 supported by the flange 300 will likewise displace parallel to the displacement axis 34 towards the frame arrangement 100. This will cause the chamber volume 510 to increase causing a negative pressure in the chamber 500 relative to the liquid environment 50. The negative pressure will drive a liquid volume, equal to the change in the chamber volume 510, through the sorbent.

The exhaust valve 620 in the exhaust 610 ensures that no liquid enters the chamber 500 through the exhaust 610.

The sorbents 750 will act as a resistance for the liquid passing through and therefore it may take ten minutes for the chamber 500 to be filled with liquid. The system 10 may hibernate during the filling of the chamber 500. The sorbents 750 will absorb or adsorb substances from the passing liquid provided that the liquid contains substances that the sorbents 750 are adapted to absorb or adsorb.

The liquid may be rejected from the chamber 500 by resetting the chamber volume 510 to the initial chamber volume 510$i$ by returning the piston crown 420 to the initial position which typically is where the chamber 500 has a minimum chamber volume 512, i.e. where the piston crown 420 is close to the liquid connection 600.

The system 10 is designed to have a small axial extent from the displacement axis 34, thereby enabling the system 10 to be inserted into a drilled bore in soil.

The space within the shell 140 is filled with liquid from the liquid environment 50, thereby the flange 300 will be exposed to the same pressure on both sides relative to the displacement axis 34 which will increase the precision of the displacement of the flange 300.

Figure 4:
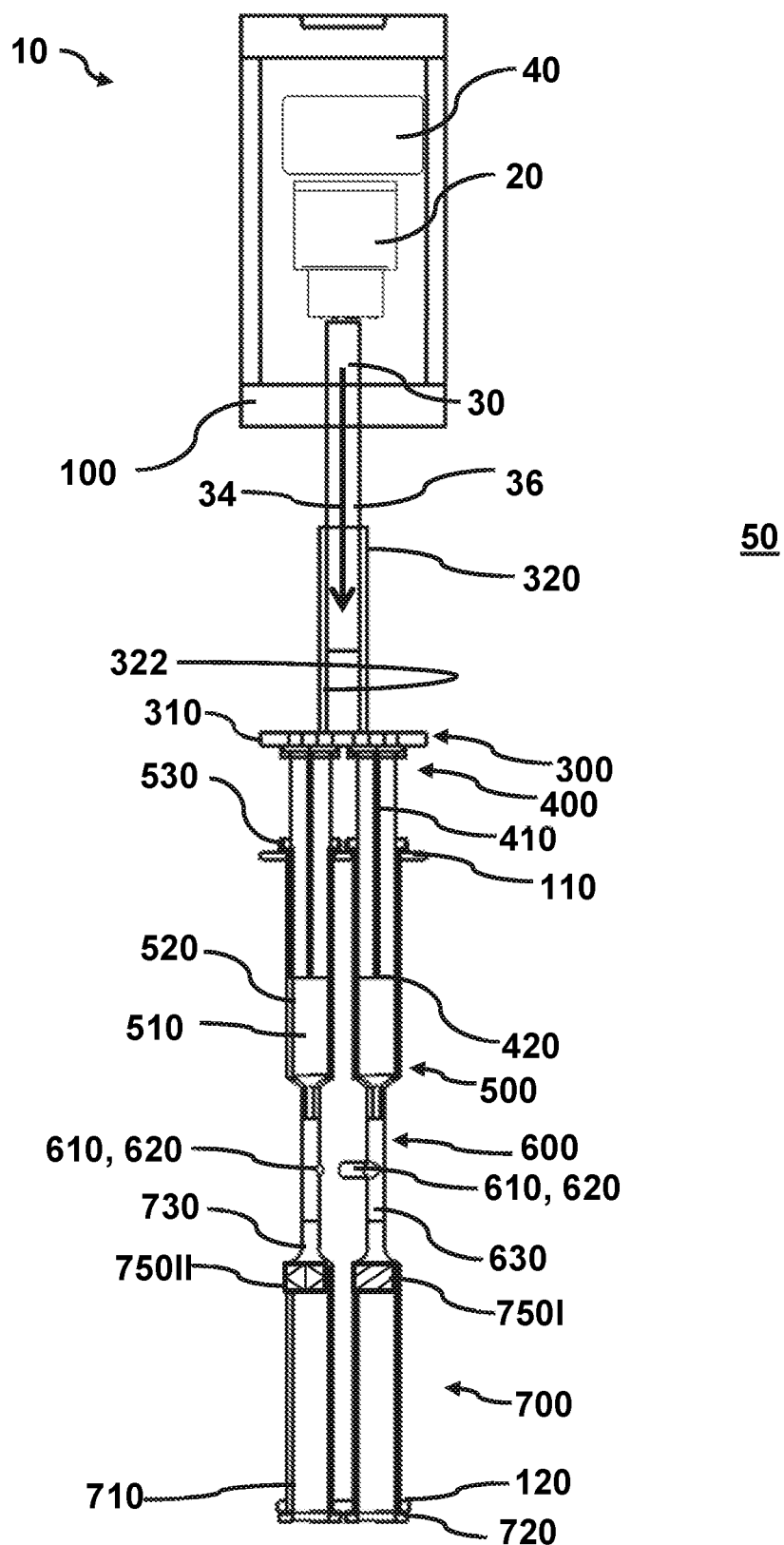
FIG. 4 illustrates a cross section of an embodiment of a system for in-situ accumulation of substances.

FIG. 4 illustrates a cross section of an embodiment of a system 10 for in-situ accumulation of substances.

The system 10 has a frame arrangement 100 supporting an actuator 20 and a battery 40 powering the actuator 20. The actuator is configured for driving the spindle 30. The spindle 30 defines a displacement axis 34 which extends in the same direction as the spindle 30.

An end of the spindle 30 is connected to a flange 300, the flange 300 has a neck 320 extending towards the actuator 20. The neck 320 has an internal thread 322 for engaging with an external thread 36 of the spindle 30. The neck 320 which has a substantial length ensures that the displacement of the flange 300 is precise with little to no twisting or flexing.

The flange 300 has a flange periphery 310 defining a shape complementary to the shell 140.

The flange 300 supports two pistons 400, each piston 400 being connected to the flange 300 by the piston foot 440, which is secured to the flange 300 using screws. Each piston 400 has a piston shaft 410 extending from the piston foot 440 to the piston crown 420.

Each piston crown 420 being configured to operate in a chamber 500. The complementary piston crowns 420 and chambers 500 define a chamber volume 510 as a function of the displacement of the piston crown 420.

Each chamber 500 has a chamber wing 530 which is used to secure the chamber 500 to a chamber plate 110.

Each chamber 500 has a chamber channel 520 adapted for displacement of the piston crown 420.

The chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600 and an inlet 710 in direct contact with liquid environment 50, when in intended use.

The cartridges 700 have two different sorbents 750I, 750II for accumulation of two different substances or two different substance groups.

The cartridges 700 are stabilised by a cartridge plate 120 fixed to the frame arrangement 100 by the shell 140.

The shell 140 has diffusion gaps 142 for diffusion of liquid from the liquid environment 50 into the system 10.

The system 10 will accumulate substances by actuating the spindle 30 causing the flange 300 to be displaced parallel to the displacement axis 34. The piston crowns 420 supported by the flange 300 will likewise displace parallel to the displacement axis 34 towards the frame arrangement 100. This will cause the chamber volume 510 to increase causing a negative pressure in the chamber 500 relative to the liquid environment 50. The negative pressure will drive a liquid volume equal to the change in the chamber volume 510 through the sorbent.

The exhaust valve 620 in the exhaust 610 ensures that no liquid enters the chamber 500 through the exhaust 610.

The sorbents 750 will act as a resistance for the liquid passing through and therefore it may take ten minutes for the chamber 500 to be filled with liquid. The system 10 may hibernate during the filling of the chamber 500. The sorbents 750 will absorb or adsorb substances from the passing liquid provided that the liquid contains substances that the sorbents 750 are adapted to absorb or adsorb.

The liquid may be rejected from the chamber 500 by resetting the chamber volume 510 to the initial chamber volume 510*i* by returning the piston crown 420 to the initial position which typically is where the chamber 500 has a minimum chamber volume 512, i.e. where the piston crown 420 is close to the liquid connection 600.

The system 10 is designed to have a small axial extent from the displacement axis 34, thereby enabling the system 10 to be inserted into a drilled bore in soil.

Figure 5:
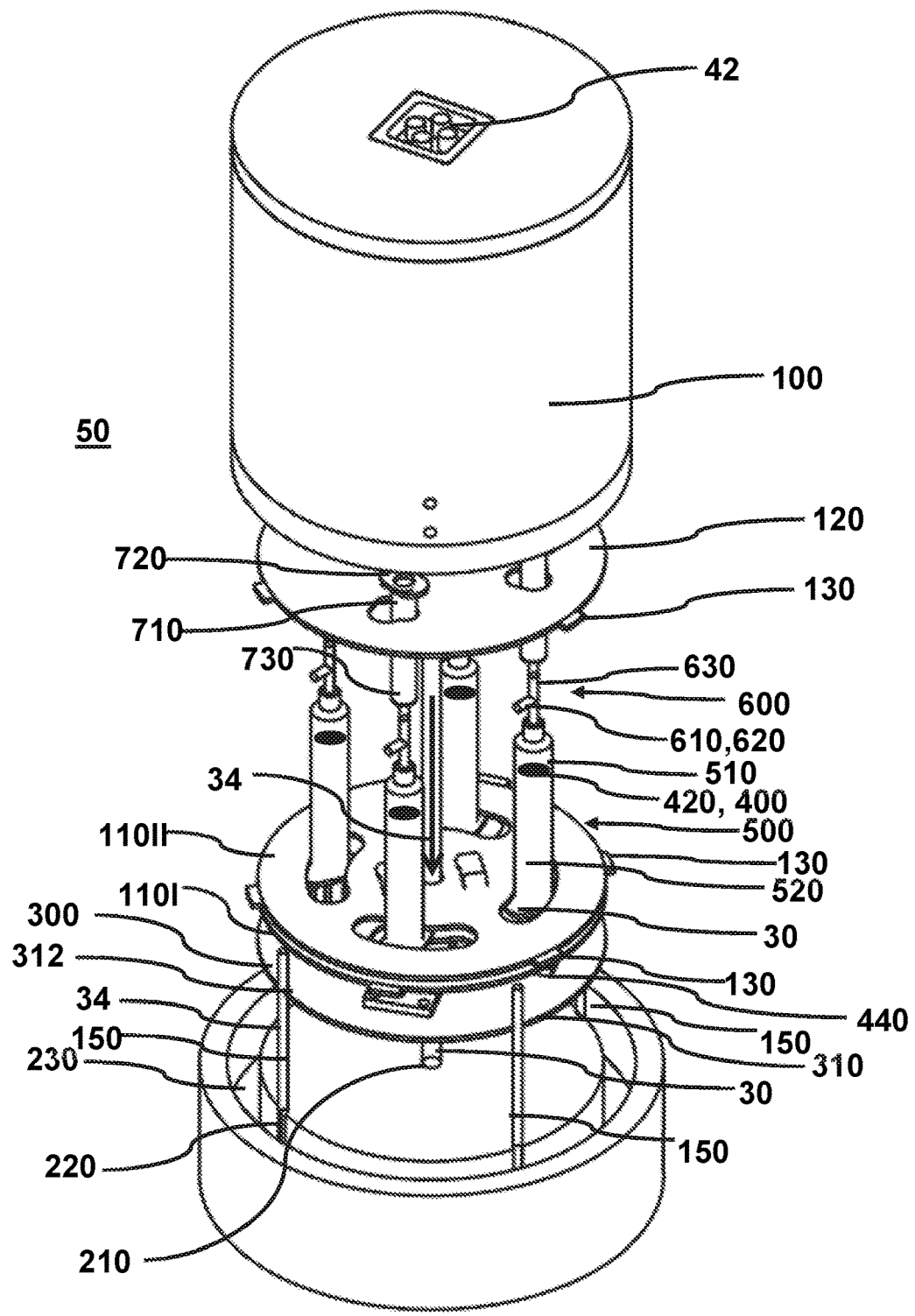
FIG. 5 illustrates a top side view of a system for in-situ accumulation of substances.

FIG. 5 illustrates a top side view of a system 10 for in-situ accumulation of substances. The system 10 has a frame arrangement 100 supporting a not shown actuator 20. The actuator 20 is configured for driving the spindle 30. The spindle 30 defines a displacement axis 34 which extends in the same direction as the spindle 30.

The spindle 30 is connected to a flange 300 by a ball screw 32 for reducing slackness.

The flange 300 has a flange periphery 310 defining a shape complementary to a shell 140 being part of the frame arrangement 100 and radially surrounding the spindle 30.

The system is disclosed without the shell 140, however, the shell 140 must be present for this specific embodiment to work as the system 10 would otherwise collapse.

The flange 300 supports four pistons 400, each piston 400 being connected to the flange 300 by a piston foot 440. The piston foot 440 is secured to the flange 300 using screws. Each piston 400 has a piston shaft 410 extending from the piston foot 440 to the piston crown 420.

The flange periphery 310 further comprises four indents 312 (two are visible) for engaging with four rods 140 (three are visible) supported longitudinally to the not shown shell 140.

Each piston crown 420 is configured to operate in a chamber 500. The piston crowns 420 and chambers 500 define a chamber volume 510 as a function of the displacement of the piston crown 420.

Each chamber 500 has a chamber wing 530 which is used to secure the chamber 500 to a first and a second chamber plate 110I, 110II by clamping. The chamber plates 110I, 110II are connected to the not shown shell 140, and thereby the chamber 500 is secured relative to the frame arrangement 100.

Each chamber 500 has a chamber channel 520 adapted for displacement of the piston crown 420.

Each chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600, an inlet 710 in direct contact with a liquid environment 50 when in intended use. The inlet has inlet wings 720.

Each cartridge 700 has a sorbent 750 (not shown) for accumulation of one or more substances or substance groups.

The cartridges 700 are stabilised by a cartridge plate 120 fixed to the frame arrangement 100 by the (not shown) shell 140.

The system 10 comprises an end plate 200 having a spindle recess 210 for engaging with the spindle 30.

The end plate 200 further comprises a shell recess 230 for engaging with the shell 140, when in intended use. The shell recess 230 forms, in this embodiment, a circular channel.

The system 10 accumulates substances by actuating the spindle 30 causing the flange 300 to be displaced parallel to the displacement axis 34. The piston crowns 420 supported by the flange 300 will likewise displace parallel to the displacement axis 34 away from the frame arrangement 100. This will cause the chamber volume 510 to increase causing a negative pressure in the chamber 500 relative to the liquid environment 50. The negative pressure will drive a liquid volume equal to the change in the chamber volume 510 through the sorbent 750.

The exhaust valve 620 in the exhaust 610 ensures that no liquid enters the chamber 500 through the exhaust 610.

The sorbent 750 will act as a resistance for the liquid passing through and therefore it may take ten minutes for the chamber 500 to be filled with liquid. The system 10 may hibernate during the filling of the chamber 500. The sorbent 750 will absorb or adsorb substances from the passing liquid provided that the liquid contains substances that the sorbent 750 is adapted to absorb or adsorb.

The liquid may be rejected from the chamber 500 by resetting the chamber volume 510 to the initial chamber volume 510*i* or by returning the piston crown 420 to the initial position which typically is where the chamber 500 has a minimum chamber volume 512, i.e. where the piston crown 420 is close to the liquid connection 600.

Figure 6:
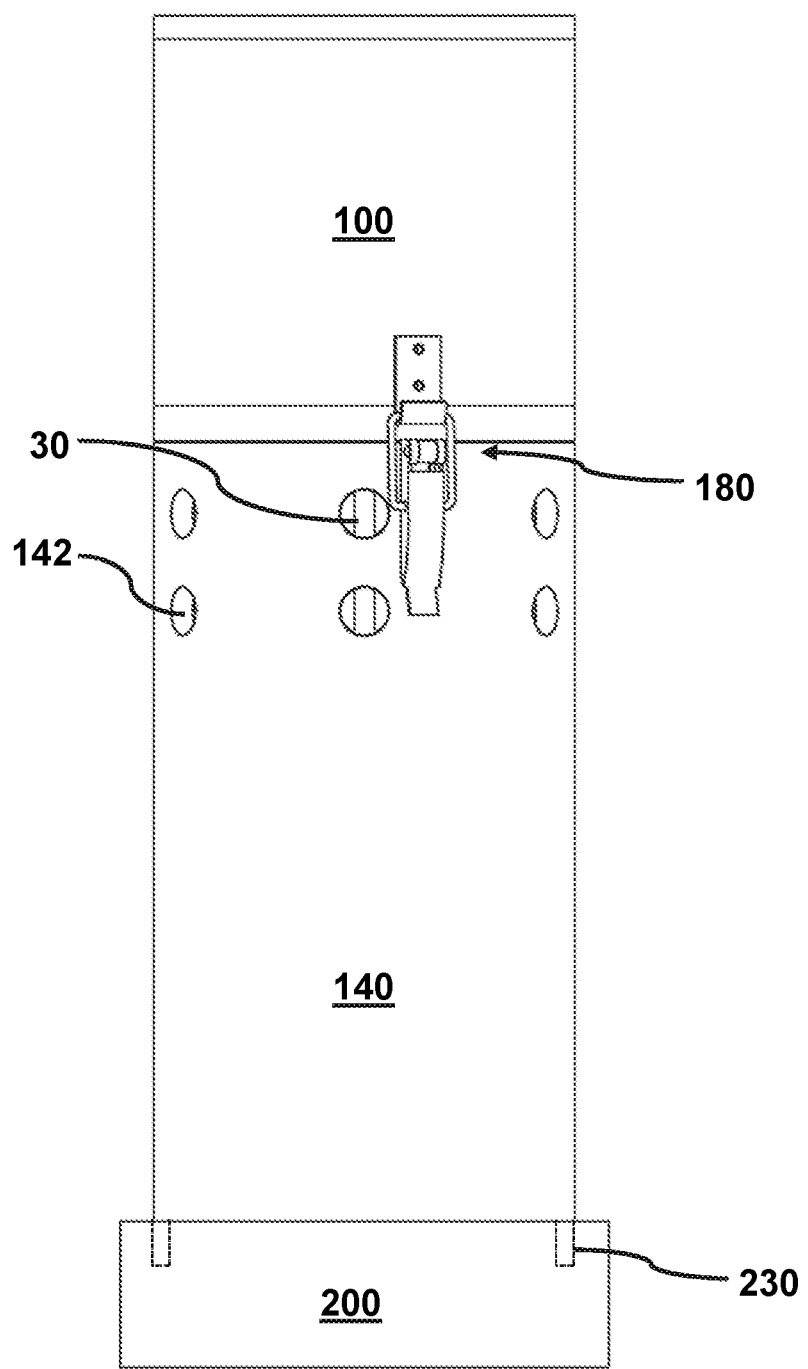
FIG. 6 illustrates a system for in-situ accumulation of substances.

FIG. 6 illustrates a system 10 for in-situ accumulation of substances.

The system 10 is identical to the system 10 disclosed in FIG. 5, but the shell 140 with diffusion gaps 142 is shown. The shell 140 is connected to the frame arrangement 100 by clamps 180 and the shell 140 is inserted into the shell recess 230 of the end plate 200.

The space within the shell 140 is filled with liquid from the liquid environment 50 thereby the flange 300 will be exposed to the same pressure on both sides relative to the displacement axis 34 which will increase the precision of the displacement of the flange 300.

FIG. 7 illustrates an embodiment of a system 10 for in-situ accumulation of substances.

FIG. 7A discloses the system 10 without a shell 140 and FIG. 7B discloses the same system 10 with a cross-section of a shell 140.

The system 10 has a frame arrangement 100 supporting a not shown actuator 20. The actuator is configured for driving the spindle 30. The spindle 30 defines a displacement axis 34 which extends in the same direction as the spindle 30.

An end of the spindle 30 is connected to a flange 300, the flange 300 has a neck 320 extending towards the not shown actuator 20. The neck 320 has a not shown internal thread 322 for engaging with an external thread 36 of the spindle 30. The neck 320 which has a substantial length ensures that the displacement of the flange 300 is precise with little to no twisting or flexing.

The flange 300 has a flange periphery 310 defining a shape complementary to the shell 140.

The flange 300 supports two pistons 400, each piston 400 being connected to the flange 300 by the piston foot 440 which is secured to the flange 300 using screws. Each piston 400 has a piston shaft 410 extending from the piston foot 440 to the piston crown 420.

Each piston crown 420 being configured to operate in a chamber 500. The complementary piston crowns 420 and chambers 500 define a chamber volume 510 as a function of the displacement of the piston crown 420. In FIG. 7B the chamber volume is at a minimum chamber volume 512 which will typically be the initial chamber volume 510i.

Each chamber 500 has a chamber wing 530 which is used to fixate the chamber 500 to a chamber plate 110. The chamber plate 110 is in FIG. 7B connected to the shell 140 and thereby the chamber 500 is fixated relative to the frame arrangement 100.

Each chamber 500 has a chamber channel 520 adapted for displacement of the piston crown 420.

The chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600, an inlet 710 in direct contact with liquid environment 50 when in intended use.

The cartridges 700 have to different sorbents 750I, 750II for accumulation of two different substances or two different substance groups.

The cartridges 700 are stabilised by a cartridge plate 120 fixed to the frame arrangement 100 by the shell 140.

The shell 140 has diffusion gaps 142 for diffusion of liquid from the liquid environment 50 into the system 10.

The system 10 will accumulate substances by actuating the spindle 30 causing the flange 300 to be displaced parallel to the displacement axis 34. The piston crowns 420 supported by the flange 300 will likewise displace parallel to the displacement axis 34 towards the frame arrangement 100. This will cause the chamber volume 510 to increase causing a negative pressure in the chamber 500 relative to the liquid environment 50. The negative pressure will drive a liquid volume, equal to the change in the chamber volume 510, through the sorbent.

The exhaust valve 620 in the exhaust 610 ensures that no liquid enters the chamber 500 through the exhaust 610.

The sorbents 750 will act as a resistance for the liquid passing through and therefore it may take 10 minutes for the chamber 500 to be filled with liquid. The system 10 may hibernate during the filling of the chamber 500. The sorbents 750 will absorb or adsorb substances from the passing liquid provided that the liquid contains substances that the sorbents 750 are adapted to absorb or adsorb.

The liquid may be rejected from the chamber 500 by resetting the chamber volume 510 to the initial chamber volume 510i by returning the piston crown 420 to the initial position which typically is where the chamber 500 has a minimum chamber volume 512, i.e. where the piston crown 420 is close to the liquid connection 600.

The system 10 is designed to have a small axial extent from the displacement axis 34, thereby enabling the system 10 to be inserted into a drilled bore in soil.

The space within the shell 140 is filled with liquid from the liquid environment 50 thereby the flange 300 will be exposed to the same pressure on both sides relative to the displacement axis 34 which will increase the precision of the displacement of the flange 300.

FIG. 8 illustrates a cross section of an embodiment of a system 10 for in-situ accumulation of substances.

The system 10 has a frame arrangement 100 supporting an actuator 20 and a battery 40 powering the actuator 20. The actuator is configured for driving the spindle 30. The spindle 30 defines a displacement axis 34 which extends in the same direction as the spindle 30.

An end of the spindle 30 is connected to a flange 300, the flange 300 has a neck 320 extending towards the actuator 20. The neck 320 has an internal thread 322 for engaging with an external thread 36 of the spindle 30. The neck 320 which has a substantial length ensures that the displacement of the flange 300 is precise with little to no twisting or flexing.

The flange 300 has a flange periphery 310 defining a shape complementary to the shell 140.

The flange 300 supports two pistons 400, each piston 400 being connected to the flange 300 by the piston foot 440 which is secured to the flange 300 using screws. Each piston 400 has a piston shaft 410 extending from the piston foot 440 to the piston crown 420.

Each piston crown 420 being configured to operate in a chamber 500. The complementary piston crowns 420 and chambers 500 define a chamber volume 510 as a function of the displacement of the piston crown 420.

Each chamber 500 has a chamber wing 530 which is used to fixate the chamber 500 to a chamber plate 110.

Each chamber 500 has a chamber channel 520 adapted for displacement of the piston crown 420.

The chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600, an inlet 710 in direct contact with liquid environment 50 when in intended use.

The cartridges 700 have two different sorbents 750I, 750II for accumulation of two different substances or two different substance groups.

The cartridges 700 are stabilised by a cartridge plate 120 fixed to the frame arrangement 100 by the shell 140.

The shell 140 has diffusion gaps 142 for diffusion of liquid from the liquid environment 50 into the system 10.

The system 10 will accumulate substances by actuating the spindle 30 causing the flange 300 to be displaced parallel to the displacement axis 34. The piston crowns 420 supported by the flange 300 will likewise displace parallel to the displacement axis 34 towards the frame arrangement 100. This will cause the chamber volume 510 to increase causing a negative pressure in the chamber 500 relative to the liquid environment 50. The negative pressure will drive a liquid volume equal to the change in the chamber volume 510 through the sorbent.

The exhaust valve 620 in the exhaust 610 ensures that no liquid enters the chamber 500 through the exhaust 610.

The sorbents 750 will act as a resistance for the liquid passing through and therefore it may take ten minutes for the chamber 500 to be filled with liquid. The system 10 may hibernate during the filling of the chamber 500. The sorbents 750 will absorb or adsorb substances from the passing liquid provided that the liquid contains substances that the sorbents 750 is adapted to absorb or adsorb.

The liquid may be rejected from the chamber 500 by resetting the chamber volume 510 to the initial chamber volume 510i by returning the piston crown 420 to the initial position which typically is where the chamber 500 has a minimum chamber volume 512, i.e. where the piston crown 420 is close to the liquid connection 600.

The system 10 is designed to have a small axial extent from the displacement axis 34, thereby enabling the system 10 to be inserted into a drilled bore in soil.

The space within the shell 140 is filled with liquid from the liquid environment 50 thereby the flange 300 will be exposed to the same pressure on both sides relative to the displacement axis 34 which will increase the precision of the displacement of the flange 300.

FIG. 9 illustrates a system 10 for in-situ accumulation of substances.

The system 10 has a frame arrangement 100 supporting a not shown actuator 20. The actuator is configured for driving the spindle 30. The spindle 30 defines a displacement axis 34 which extends in the same direction as the spindle 30.

The spindle 30 is connected to a flange 300 by a ball screw 32 for reducing slackness.

The flange 300 has a flange periphery 310 defining a shape complementary to a shell 140 being part of the frame arrangement 100 and radially surrounding the spindle 30.

The shell 140 has diffusion gaps 142 for diffusion of liquid between the liquid environment 50 and the system 10.

The flange 300 supports four pistons 400, each piston 400 being connected to the flange 300 by the piston foot 440 which may be secured to the flange 300 using screws. Each piston 400 has a piston shaft 410 extending from the piston foot 440 to the piston crown 420 and the piston crown 420 has a piston ring 430.

The flange periphery 310 further comprises four not shown indents 312 for engaging with four rods 150 (only one is shown) longitudinally supported to the shell 140.

Each piston crown 420 is configured to operate in a chamber 500.

In the present figure only one piston crown 420 operates in the chamber 500. The piston crown 420 and chamber 500 define a chamber volume 510 as a function of the displacement of the piston crown 420.

The chamber 500 has a chamber wing 530 which is used to fixate the chamber 500 to a first and a second chamber plate 110I, 110II by clamping. The chamber plates 110I, 110II are connected to the shell 140, and thereby the chamber 500 is fixated relative to the frame arrangement 100.

The chamber 500 has a chamber channel 520 adapted for displacement of the piston crown 420.

The chamber 500 is in a liquid connection 600 with a cartridge 700. The liquid connection 600 has an exhaust 610 with an exhaust valve 620 and a cartridge valve 630 near the cartridge 700.

The cartridge 700 comprises a cartridge outlet 730 connected to the liquid connection 600, an inlet 710 in direct contact with liquid environment 50 when in intended use. The inlet has inlet wings 720.

The cartridge 700 has a sorbent 750 for accumulation of one or more substances or substance groups.

The cartridges 700 are stabilised by a cartridge plate 120 fixed to the frame arrangement 100 by the shell 140.

The system 10 comprises an end plate 200 having a (not shown) spindle recess 210 for engaging with the spindle 30.

The end plate 200 further comprises (not shown) a shell recess 230 for engaging with the shell 140.

The system 10 accumulates substances by actuating the spindle 30 causing the flange 300 to be displaced parallel to the displacement axis 34. The piston crowns 420 supported by the flange 300 will likewise displace parallel to the displacement axis 34 away from the frame arrangement 100. This will cause the chamber volume 510 to increase causing a negative pressure in the chamber 500 relative to the liquid environment 50. The negative pressure will drive a liquid volume equal to the change in the chamber volume 510 through the sorbent 750.

The exhaust valve 620 in the exhaust 610 ensures that no liquid enters the chamber 500 through the exhaust 610.

The sorbent 750 will act as a resistance for the liquid passing through and therefore it may take ten minutes for the chamber 500 to be filled with liquid. The system 10 may hibernate during the filling of the chamber 500. The sorbent 750 will absorb or adsorb substances from the passing liquid provided that the liquid contains substances that the sorbent 750 is adapted to absorb or adsorb.

The liquid may be rejected from the chamber 500 by resetting the chamber volume 510 to the initial chamber volume 510i by returning the piston crown 420 to the initial position which typically is where the chamber 500 has a minimum chamber volume 512, i.e. where the piston crown 420 is close to the liquid connection 600.

FIG. 10 illustrates a top side view of a system 10 for in-situ accumulation of substances.

The system 10 has a frame arrangement 100 supporting a not shown actuator 20. The actuator 20 is configured for driving the spindle 30. The spindle 30 defines a displacement axis 34 which extends in the same direction as the spindle 30.

The spindle 30 is connected to a flange 300 by a ball screw 32 for reducing slackness.

The flange 300 has a flange periphery 310 defining a shape complementary to a shell 140 being part of the frame arrangement 100 and radially surrounding the spindle 30. The system 10 is disclosed without the shell 140, however the shell 140 must be present for this specific embodiment to work as the system 10 would otherwise collapse.

The flange 300 supports four pistons 400, each piston 400 being connected to the flange 300 by a piston foot 440. The piston foot 440 is secured to the flange 300 using screws. Each piston 400 has a piston shaft 410 extending from the piston foot 440 to the piston crown 420.

The flange periphery 310 further comprises four indents 312 (two are visible) for engaging with four rods 150 (three are visible) longitudinally supported to the not shown shell 140.

Each piston crown 420 are configured to operate in a chamber 500. The piston crowns 420 and chambers 500 define a chamber volume 510 as a function of the displacement of the piston crown 420.

Each chamber 500 has a chamber wing 530 which is used to fixate the chamber 500 to a first and a second chamber plate 110I, 110II by clamping. The chamber plates 110I, 110II are connected to the not shown shell 140, and thereby the chamber 500 is fixated relative to the frame arrangement 100.

Each chamber 500 has a chamber channel 520 adapted for displacement of the piston crown 420.

Each chamber 500 is in a liquid connection 600 with a cartridge 700. The liquid connection 600 has an exhaust 610 with an exhaust valve 620 and a cartridge valve 630 near the cartridge 700.

Each cartridge 700 comprises a cartridge outlet 730 connected to the liquid connection 600, an inlet 710 in direct contact with liquid environment 50 when in intended use. The inlet has inlet wings 720.

Each cartridge 700 has a sorbent 750 (not shown) for accumulation of one or more substances or substance groups.

The cartridges 700 are stabilised by a cartridge plate 120 fixed to the frame arrangement 100 by the (not shown) shell 140.

The system 10 comprises an end plate 200 having a spindle recess 210 for engaging with the spindle 30.

The end plate 200 further comprises a shell recess 230 for engaging with the shell 140 when in intended use. The shell recess 230 forms, in this embodiment, a circular channel.

The system 10 accumulates substances by actuating the spindle 30 causing the flange 300 to be displaced parallel to the displacement axis 34. The piston crowns 420 supported by the flange 300 will likewise displace parallel to the displacement axis 34 away from the frame arrangement 100. This will cause the chamber volume 510 to increase causing a negative pressure in the chamber 500 relative to the liquid environment 50. The negative pressure will drive a liquid volume equal to the change in the chamber volume 510 through the sorbent 750.

The exhaust valve 620 in the exhaust 610 ensures that no liquid enters the chamber 500 through the exhaust 610.

The sorbent 750 will act as a resistance for the liquid passing through and therefore it may take ten minutes for the chamber 500 to be filled with liquid. The system 10 may hibernate during the filling of the chamber 500. The sorbent 750 will absorb or adsorb substances from the passing liquid provided that the liquid contains substances that the sorbent 750 is adapted to absorb or adsorb.

The liquid may be rejected from the chamber 500 by resetting the chamber volume 510 to the initial chamber volume 510i or by returning the piston crown 420 to the initial position which typically is where the chamber 500 has a minimum chamber volume 512, i.e. where the piston crown 420 is close to the liquid connection 600.

FIG. 11 illustrates a system 10 for in-situ accumulation of substances.

The system 10 is identical to the system 10 disclosed in FIG. 10, but the shell 140 with diffusion gaps 142 is shown. The shell 140 is connected to the frame arrangement 100 by clamps 180 and the shell 140 is inserted into the shell recess 230 of the end plate 200.

The space within the shell 140 is filled with liquid from the liquid environment 50 thereby the flange 300 will be exposed to the same pressure on both sides relative to the displacement axis 34 which will increase the precision of the displacement of the flange 300.

FIG. 12 illustrates a spindle 30 with a flange 300 supporting four pistons 400 connected to chambers 500.

FIG. 12A-C discloses the same setup, but in FIG. 12B the setup has a minimum chamber volume 512, and in FIG. 12C the setup has a maximum chamber volume 514.

The spindle 30 defines the displacement axis 34. The flange 300 is connected to the spindle 30 by a screw ball 32.

The flange 300 has a flange periphery 510 with four indents 312 for engaging with not shown rods 150, thereby increasing the stability.

The flange 300 supports four pistons 400 positioned symmetrically relative to the displacement axis 34. Each piston 400 is connected by a piston foot 440 to the flange 300. A piston shaft 410 extends from each piston foot 440 to a piston crown 420.

Each piston crown 420 operates in a chamber 500, thereby defining a chamber volume 510.

Each chamber 500 has a chamber channel 520 adapted for displacement of the piston crown 420 and chamber wing 530 for engaging with one or two (not shown) chamber plates 110.

FIG. 13 illustrates setup of a piston 400, a chamber 500, a liquid connection 600 and a cartridge 700.

The piston 400 comprises a piston shaft 410 extending from piston feet 440 to a distal piston crown 420. The piston crown 420 is configured to cooperate in the chamber 500, thereby defining a chamber volume 510. The chamber 500 having a chamber channel 520 for displacement of the piston crown 420.

The chamber 500 further comprises a chamber wing 530 for engaging with one or two not shown chamber plates 110.

The chamber 500 is connected to the cartridge 700 by the liquid connection 600. The liquid connection 600 comprises an exhaust 610 with a one way exhaust valve 620 and a one way cartridge valve 630 close to the cartridge 700, such that liquid may only enter the chamber 500 through the cartridge 700 and may only exit the chamber 500 through the exhaust 610.

FIG. 14 illustrates a cross section of a shell 140.

The shell 140 is a circular, hollow cylinder. The displacement axis 34 is shown for providing a reference for the placement of the different technical features.

The shell 140 is adapted for the system 10 otherwise disclosed FIG. 10.

The shell 140 has diffusion gaps 142 for diffusion of liquid between the internal parts of the shell 140 or system 10 and the liquid environment. The diffusion gaps 142 have a size, such that the liquid in the system 10 has been replaced between two acts of driving a liquid volume through the sorbent.

The diffusion gaps 142 are positioned near where the cartridge 700 would be placed as the liquid is collected from and around the cartridge 700.

The shell 140 has three cartridge plate channels 170, but only two cartridge plate channels 170 are shown in the cross section of the shell 140. The cartridge plate channels 170 are adapted for receiving and holding a male connection 130 of a cartridge plate 120. An embodiment of the cartridge plate 120 is disclosed in FIG. 17. The cartridge plate channels 170 are configured for allowing the cartridge plate 120 to rotate slightly.

The shell 140 has three first chamber plate channels 160I, although only two are shown in the cross-section. The three first chamber plate channels 160I are adapted for receiving and holding male connections 130 of a first chamber plate 110I. An embodiment of the first chamber plate 110I is disclosed in FIG. 18.

The shell 140 has three second chamber plate channels 160II, although only two are shown in the cross-section. The three second chamber plate channels 160II are adapted for receiving and holding male connections 130 of a second chamber plate 110II. An embodiment of the second chamber plate 110II is disclosed in FIG. 19.

The first chamber plate channels 160I are slightly offset from the second chamber plate channels 160II relative to the displacement axis 34, such that the first chamber plate 110I and the second chamber plate 110II can fixate one or more chambers 500 to the shell 140 and through the shell 140 to the frame arrangement when in intended use. The chamber plates 110I, 110II fixate the chambers 500 by clamping chamber wings 530.

The chamber channels 160I, 160II have lock arrangements 162 for fixating the male connections 130. The chamber plates 110I, 110II are locked in the lock arrangements 162 by inserting the male connections 140 of the chamber plates 110I, 110II into the chamber channels 160I, 160II and moving the chamber plates 110I, 110II along the chamber channels 160I, 160II to an end. The chamber plates 110I, 110II are then turned, then lifted, then turned again and then moved to an innermost part of the lock arrangements 162. The male connections 130 of the chamber plates 110I, 110II will then be confined.

The shell 140 is equipped with four rods 150 although only two are shown in the cross section.

The rods 150 are adapted for interacting with indents 312 in a periphery 310 of a flange 300 when in intended use. Thereby, the flange 300 moves more stable and precise.

FIG. 15 illustrates end plate 200 in a side view (A) and a top view (B).

The end plate 200 has a spindle recess 210 for receiving and thereby stabilising a spindle 30.

The end plate 200 has a shell recess 230 for receiving a shell 140. In this embodiment the shell recess 230 forms a channel radially surrounding the spindle recess 210.

The shell recess 230 is equipped with four bores 220 for receiving and further stabilising rods 150 otherwise longitudinal supported by the shell 140.

FIG. 16 illustrates an actuator 20 and battery 40 from a top view (A), a side view (B), and bottom view (C).

FIG. 16 discloses how the battery 40 and the actuator 20 are typically arranged when supported by a frame arrangement 100. The battery 40 is connected to a plug 42 for charging of the battery 40.

FIG. 17 illustrates a cartridge plate 120.

The cartridge plate 120 has a substantially circular shape with a centrally positioned cartridge plate spindle bore 124 for a spindle 30 to go through.

The cartridge plate 120 has three male connections 130 for securing the cartridge plate 120 to a shell 140 having a cartridge plate channel 170.

The cartridge plate 120 has four cartridge plate apertures 122 for stabilising up to four cartridges 700. The shape of the four cartridge plate apertures 122 is adapted for receiving different cartridges 700 having different shapes.

FIG. 18 illustrates a first chamber plate 110I from a top view (A), a bottom view (B), and top side view (C).

The first chamber plate 110I is adapted to be positioned below a second chamber plate 110II, wherein the chamber plates 110I, 110II interact with at least one chamber wing 530 positioned between the chamber plates 110I, 110II.

The first chamber plate 110I has a substantially circular shape with a centrally positioned chamber plate spindle bore 114 for a spindle 30 to go through.

The first chamber plate 110I has three male connections 130 for securing the first chamber plate 110I to a shell 140 having a first chamber plate channel 160I.

The first chamber plate 110I has four chamber plate apertures 112 for fixating up to four chambers 700.

The shape of the four chamber plate apertures 112 is adapted for being inserted into the first chamber plate channel 160I after one or more chambers 500 have been installed in the system 10. Therefore, the chamber plate apertures 112 are adapted for moving past a chamber 500 with chamber wings 530.

Each of the chamber plate apertures 112 has a chamber plate aperture recess 113 extending radially relative to the chamber plate spindle bore 114 for enabling the first chamber plate 110I to be locked in a lock arrangement 162 of the first chamber plate channel 160I by rotation.

FIG. 19 illustrates a second chamber plate 110II from a top view (A), a bottom view (B), and top side view (C).

The second chamber plate 110II is adapted to be positioned above a first chamber plate 110I, wherein the chamber plates 110I, 110II interact with at least one chamber wing 530 positioned between the chamber plates 110I, 110II.

The second chamber plate 110II has a substantially circular shape with a centrally positioned chamber plate spindle bore 114 for a spindle 30 to go through.

The second chamber plate 110II has three male connections 130 for securing the second chamber plate 110II to a shell 140 having a second chamber plate channel 160II.

The second chamber plate 110II has four chamber plate apertures 112 for fixating up to four chambers 500.

The shape of the four chamber plate apertures 112 is adapted for being inserted into the second chamber plate channel 160I after one or more chambers 500 and the first chamber plate 110I has been installed in the system 10. Therefore, the chamber plate apertures 112 should only be able to move past part of the chamber 500.

Each of the chamber plate apertures 112 has a shape, which extends radially relative to the chamber plate spindle bore 114 for enabling the second chamber plate 110II to be locked in a lock arrangement 162 of the second chamber plate channel 160II by rotation.

The invention claimed is:

1. A method for in-situ accumulation of one or more substances from a liquid environment, the method including the steps of:
    placing a frame arrangement comprising a shell, a chamber, and a cartridge with an inlet in the liquid environment, wherein the shell at least partly surrounds the cartridge and the cartridge comprises a sorbent, wherein the sorbent is adapted for accumulating a specific substance or a specific group of substances, wherein the shell has diffusion gaps for diffusion of liquid from the liquid environment into the shell, such that the inlet of the cartridge is in direct contact with the diffused liquid from the liquid environment;
    driving a liquid volume through the sorbent by negative pressure; and
    repeating the act of driving as a function of time.

2. The method according to claim 1, wherein the act of driving is performed by changing a volume of the chamber having an initial chamber volume in liquid connection with the cartridge.

3. The method according to claim 2, wherein the act of driving is performed by increasing the chamber volume of the chamber.

4. The method of claim 2, wherein the act of driving is performed by a pressure difference at the chamber relative to the liquid environment, while the chamber has a fixed chamber volume.

5. The method of claim 2, wherein the act of driving includes resetting the chamber to the initial chamber volume.

6. The method of claim 1, wherein the act of repeating includes an act of hibernating as a function of time between the acts of driving.

7. The method according to claim 6, wherein the act of hibernating is performed for a hibernation time being between 0.1-24 hours, 0.1-10 hours, 0.5-5 hours, 0.75-3.5 hours, or 1-2 hours.

8. The method of claim 1, wherein the method is performed over a period of 0.1-3 months, 0.5-2 months or 0.75-1.5 months, or 1 month.

9. A system for in-situ accumulation of one or more substances from a liquid environment, the system comprising:
    a frame arrangement comprising a shell, and a cartridge with an inlet, wherein the frame arrangement is configured for supporting an actuator configured to drive a spindle defining a displacement axis, the spindle coupled to a flange, wherein the shell at least partly surrounds the cartridge, the cartridge comprises a sorbent adapted for accumulating a specific substance or a specific group of substances, and wherein the shell has diffusion gaps for diffusion of the liquid from the liquid environment into the shell, such that the inlet of the cartridge is in direct contact with the diffused liquid from the liquid environment;

the flange configured for a displacement along the displacement axis, the flange supporting a piston crown configured to operate in a chamber;

the chamber defining a chamber volume as a function of the piston crown, the chamber having means for being secured to the frame arrangement, and being in a liquid connection with the cartridge, wherein the act of driving a liquid volume through the sorbent by negative pressure is performed by changing a volume of the chamber having an initial chamber volume; and a means configured and arranged to repeat the act of driving as a function of time.

10. The system of claim 9, wherein the system further including two or more piston crowns, two or more chambers, and two or more cartridges positioned symmetrically around the displacement axis.

11. The system of claim 9, wherein the liquid connection includes an exhaust configured and arranged for expelling liquid from the chamber.

12. A non-transitory computer program comprising instructions to cause the system, according to claim 9, to execute the acts of the method according to claim 1.

13. A non-transitory computer-readable medium having stored thereon the computer program of claim 12.

* * * * *